United States Patent
O'Dowd et al.

(10) Patent No.: US 9,714,244 B2
(45) Date of Patent: Jul. 25, 2017

(54) SUBSTITUTED PYRIDO[4,3-D]PYRIMIDINES AS WEE-1 INHIBITORS

(71) Applicant: ALMAC DISCOVERY LIMITED, Craigavon (GB)

(72) Inventors: Colin Roderick O'Dowd, Craigavon (GB); James Samuel Shane Rountree, Craigavon (GB); Frank Burkamp, Craigavon (GB); Andrew John Wilkinson, Craigavon (GB)

(73) Assignee: ALMAC DISCOVERY LIMITED, Craigavon (GB)

( * ) Notice: Subject to any disclaimer, the term of this patent is extended or adjusted under 35 U.S.C. 154(b) by 0 days.

(21) Appl. No.: 14/783,752

(22) PCT Filed: Apr. 11, 2014

(86) PCT No.: PCT/GB2014/051136
§ 371 (c)(1),
(2) Date: Oct. 9, 2015

(87) PCT Pub. No.: WO2014/167347
PCT Pub. Date: Oct. 16, 2014

(65) Prior Publication Data
US 2016/0060258 A1     Mar. 3, 2016

(30) Foreign Application Priority Data
Apr. 11, 2013 (GB) .................................. 1306610.5

(51) Int. Cl.
| | | |
|---|---|---|
| *A61K 31/519* | (2006.01) | |
| *C07D 471/04* | (2006.01) | |
| *A61K 31/5377* | (2006.01) | |
| *A61K 31/541* | (2006.01) | |

(52) U.S. Cl.
CPC .......... *C07D 471/04* (2013.01); *A61K 31/519* (2013.01); *A61K 31/5377* (2013.01); *A61K 31/541* (2013.01)

(58) Field of Classification Search
CPC ............................ A61K 31/519; C07D 471/04
USPC ...................... 514/264.11; 544/117, 279, 362
See application file for complete search history.

(56) References Cited

U.S. PATENT DOCUMENTS

| | | | |
|---|---|---|---|
| 2011/0245229 A1 | 10/2011 | Bamba et al. | |
| 2013/0023523 A1 | 1/2013 | Zhu et al. | |
| 2013/0225589 A1* | 8/2013 | Woods .................. | C07D 471/04 514/243 |

FOREIGN PATENT DOCUMENTS

WO    2013/126656 A1    8/2013

OTHER PUBLICATIONS

Jordan, V. C. Nature Reviews: Drug Discovery, 2, 2003, 205.*
Hackam, et al. JAMA, 296(14), 2006, 1731-1732.*
International Preliminary Report on Patentability corresponding to International Patent Application No. PCT/GB2014/051136, issued Oct. 13, 2015.
International Search Report corresponding to International Patent Application No. PCT/GB2014/051136, mailed Jun. 11, 2014.

* cited by examiner

*Primary Examiner* — Douglas M Willis
(74) *Attorney, Agent, or Firm* — Brian C. Trinque; Lathrop & Gage LLP

(57) ABSTRACT

The present invention relates to compounds of formula (I) that are useful as inhibitors of the activity of Wee-1 kinase. The present invention also relates to pharmaceutical compositions comprising these compounds and to methods of using these compounds in the treatment of cancer and methods of treating cancer.

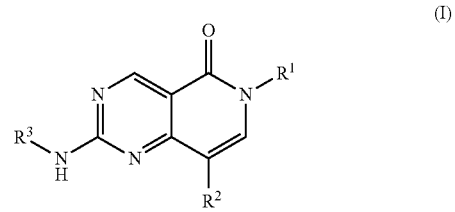

11 Claims, No Drawings

SUBSTITUTED PYRIDO[4,3-D]PYRIMIDINES AS WEE-1 INHIBITORS

RELATED APPLICATIONS

This application is a 35 U.S.C. §371 filing of International Application No. PCT/GB2014/051136, filed Apr. 11, 2014, which claims priority to Great Britain Patent Application No. 1306610.5, filed Apr. 11, 2013, each of which are incorporated herein by reference in their entireties.

The present invention relates to compounds that are useful as inhibitors of the activity of Wee-1 kinase. The present invention also relates to pharmaceutical compositions comprising these compounds and to methods of using these compounds in the treatment of cancer and methods of treating cancer.

BACKGROUND TO THE INVENTION

Cells are continually challenged on a daily basis, resulting in multiple lesions forming in DNA. The lesions, if not repaired, can lead to mutations or cell death, thus complex signalling networks exist which ensure that lesions are detected, and repaired to maintain the integrity of DNA.

Detection of DNA damage initiates a series of events which are key in maintaining the genome. Cell cycle checkpoints are designed to stop the cell cycle and allow repair of the lesion before allowing the cell to continue into mitosis.

Two key checkpoints have been identified, one at the end of G1 phase and the second at G2, which work in tandem to ensure all lesions, are identified and repaired. In 50% of human cancers the G1 checkpoint is non-functional due to mutations in the tumour suppressor gene p53. However, the G2 check-point is seldomly mutated, and often found to be activated in cancer cells. Cancer cells exploit this to confer resistance to treatment modalities including DNA damaging agents and radiation.

Three kinases have been identified as key regulators of the G2 checkpoint, namely Chk1, Chk2 and Wee-1. Inhibitors for the kinases are currently in clinical trials.

Wee-1 is a nuclear tyrosine kinase, which negatively regulates entry into mitosis, at the G2/M check-point by catalysing a phosphorylation of the cdc2/cyclin B kinase complex. The phosphorylation occurs on the Tyrosine 15 residue and leads to the inactivation of cdc2/cyclin B complex ultimately preventing mitosis. Wee-1 function is intimately linked to that of Chk1 and Chk2 due to their phosphorylation and inactivation of cdc25 on serine 216, as well as the reported activation of Wee-1 by Chk 1 & 2 (Ashwell et al., 2012, *DNA Repair in Cancer Therapy, DOI: 10.1016/B978-0-12-384999-1.10010-1*).

Wee-1 is downstream of the Chk family and is a crucial component of the checkpoint signalling cascade as it prevents cells from entering mitosis if lesions are detected.

Commonly administered anti-cancer compounds induce DNA damage; including anti-metabolites, platiniums, topoisomerase inhibitors and alkylating agents. However, their efficacy is limited due to excessive toxicity, resistance and lack of tumour selectivity. Compounds which work in combination with these agents to prevent DNA repair selectively in tumour cells would be extremely beneficial. The tumour suppressor gene p53 is commonly mutated in tumour cell lines, therefore the administration of a Wee-1 kinase inhibitor, which will abrogate the G2 check point, may lead to increased sensitivity to DNA damaging agents. The potential for this has been reported, silencing of Wee-1 activity was sufficient to sensitize HeLa cells to doxorubicin due to abrogation of G2 arrest. In contrast, in normal breast epithelium which have a fully complement p53, the removal of Wee-1 function had little additional effect compared to doxorubicin alone (Wang et al., 2004, Cancer Biology and Therapy, 3(3), 305-313).

It has been reported that cell lines harbouring mutations in the tumour suppressor gene p53 have increased sensitivity to DNA damaging agents when co-administered with Wee-1 small molecule inhibitors. In vitro and in vivo efficacy has been reported when small molecule inhibitors are combined with gemcitabine, 5-fluorouracil, carboplatin, cisplatin (Hirai et al 2010, Cancer Biology & Therapy 9:7, 514-522), cytarabine (Tibes et al., 2012, Blood, 119(12), 2863-2872) and Src inhibitors (Cozzi et al., 2012, Cell Cycle 11(5), 1-11). Single agent apoptotic efficacy, independent of p53 status, has been reported in sarcoma cell lines and in patient derived sarcoma samples (Kreahling et al., 2012, Mol. Cancer Ther., 11(1), 174-182).

Irradiation is known to increase phosphorylation of the Tyr15 and Thr14 residues of cdc2, leading to a radioresistant phenotype. Inhibition of Wee-1 activity by small molecules (Wang et al., 2004, Cancer Biology and Therapy 3(3), 305-313) leads to a reduction in phosphorylation and radiosensitization effect, with the effect more pronounced in p53 mutant cell lines.

Compounds having a kinase inhibitory effect, for example a Wee-1 kinase inhibitory effect, are described in WO 2007/126122, US 2010/0063024, EP 2,213,673, WO 2008/133866 and US 2007/0254892.

WO 2010/067886, WO 2010/067888, US 2011/0135601, EP 2,168,966, WO 2005/090344, US 2009/0048277 and Bioorg. Med. Chem. Lett., 2005, 15, 1931-1935 describe various compounds such as dihydropyrimidopyrimidine and pyridopyrimidinone derivatives having a kinase inhibitory effect. In particular, the compounds of WO 2005/090344 are said to show activity as protein kinase inhibitors, in particular Src family tyrosine kinase inhibitors. The compounds described in Bioorg. Med. Chem. Lett., 2005, 15, p 1931-1935 are said to be 10-100-fold more potent inhibitors of c-Src than Wee-1, and variation of substituents on the 6-phenyl ring does not markedly alter this preference. It is said that solubilizing substituents off the 2-anilino ring in many cases increases Wee-1 activity, lowering this preference to about 10-fold. 5-Alkyl substituted analogues are said to be generally Wee-1 selective, but at the expense of absolute potency.

WO 2013/013031 describes pyridazino[4,5-d]pyrimidin-(6H)-one inhibitors of Wee-1 kinase which are said to be useful for inhibiting kinases such as Wee-1 and in methods of treating diseases such as cancer. Compounds within the scope of disclosure of WO 2013/013031 have a nitrogen atom at the '3-position' of the ring relative to the carbonyl group.

US 2013/0018045 describes various tricyclic 2-sulfonamide compounds which are useful for inhibiting kinases such as Wee-1 and methods of treating diseases such as cancer. Compounds within the scope of disclosure of US 2013/0018045 have a sulfonamide group at the '1-position' on the ring and the atoms at the '3- and 4-positions' form part of a fused aryl or heteroaryl ring (A).

It is one object of the present invention to overcome at least some of the disadvantages of the prior art or to provide a commercially useful alternative thereto.

It is a further object of the present invention to provide a compound having an improved selectivity towards Wee-1 kinase compared to known compounds or compositions.

It is a further object of the present invention to provide a compound having an improved stability in human microsomes, for example human liver microsomes, compared to known compounds or compositions.

It is a further object of the present invention to provide a compound having an enhanced or similar kinase-inhibitory effect compared to known compounds or compositions.

It is a further object of the present invention to provide a compound having an improved efficacy compared to known compounds or compositions.

It is a further object of the present invention to provide a compound having an improved efficacy and tolerability when administered in combination with other therapies compared to known compounds or compositions.

It is a further object of the present invention to provide a compound having an improved tolerability compared to known compounds or compositions.

SUMMARY OF THE INVENTION

In a first aspect the present invention provides a compound of Formula (I):

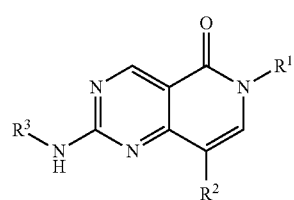

(I)

or a pharmaceutically acceptable salt or N-oxide derivative thereof, wherein:

$R^1$ is an optionally substituted aryl or heteroaryl group;

$R^2$ is a hydrogen atom, a halo group, a cyano group, or an optionally substituted aryl, alkyl, alkenyl, alkynyl, cycloalkyl, cycloalkenyl, heterocyclyl, amino or amido group;

$R^3$ is an optionally substituted aryl, alkyl, alkenyl, alkynyl, cycloalkyl, cycloalkenyl or heterocyclyl group.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a second aspect the present invention provides a pharmaceutical composition comprising the compound of formula (I), or a pharmaceutically acceptable salt or N-oxide derivative thereof, and at least one pharmaceutically acceptable excipient.

In a third aspect the present invention provides the compound of formula (I), or a pharmaceutically acceptable salt or N-oxide derivative thereof, or a pharmaceutical composition comprising the compound of formula (I) for use in therapy.

In a fourth aspect the present invention provides the compound of formula (I) for use as a medicament.

In a fifth aspect the present invention provides the compound of formula (I) for use in treating or preventing cancer.

In a sixth aspect the present invention provides the compound of formula (I) for the manufacture of a medicament for treating or preventing cancer.

In a seventh aspect the present invention provides the use of the compound of formula (I) for the manufacture of a medicament for treating or preventing cancer.

In an eighth aspect the present invention provides a method of treating or preventing cancer in a human or animal patient comprising administering to a patient in need thereof an effective amount of the compound of formula (I) or a pharmaceutical composition comprising the compound of formula (I).

Other preferred embodiments of the compounds according to the invention appear throughout the specification and in particular in the examples. Particularly preferred are those named compounds having greater activity as tested. Compounds having higher activity are more preferred over those having lower activity.

The present inventors have surprisingly found that the compounds of the present invention show an improved selectivity towards Wee-1 kinase. Preferably, in particular, the compounds of the invention are selective over members of the Src family of kinases, for example LCK (Lymphocyte specific protein tyrosine kinase) and c-Src. Unexpectedly, the compounds of the present invention also appear to show greater selectivity than a representative compound described in Bioorg. Med. Chem. Lett., 2005, 15, 1931-1935 (see Examples) and compounds described in WO 2013/013031 and US 2013/0018045.

The present inventors have surprisingly found that the compounds of the present invention also show reduced or comparable hERG inhibition, improved or comparable human liver microsome stability and reduced or comparable CVS toxicity compared to the kinase inhibitors of the prior art.

Without wishing to be bound by theory it is thought that the compounds of the present invention tend to show an improved selectivity over other off-target kinases due, at least in part, to the position of the carbonyl (C=O) group as shown in formula (I), that is, the carbonyl group adjacent to the nitrogen atom to which $R^1$ is attached.

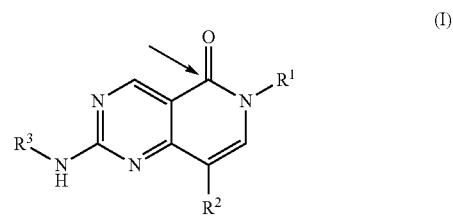

(I)

Further factors which result in the improved selectivity over other off-target kinases, as well as improved hERG activity values, improved human liver microsome stability and reduced CVS toxicity, include the structural relationship between the carbonyl (C=O) group, the N—$R^1$ group at the '2-position' on the ring, the C—H at the '3-position' and the C—$R^2$ group at the '4-position'.

For example, representative compounds of the present invention have surprisingly been found to exhibit reduced hERG inhibition and reduced CVS toxicity compared to equivalent compounds within the scope of WO 2013/013031 which have a nitrogen atom at the '3-position' on the ring:

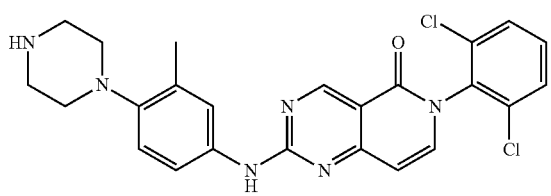

Example 7 of the present invention
Wee1/pCDC2 IC$_{50}$ (nM): 3.3/49.7
KSol (µM): 174 (avg. 157/190)
hERG IC$_{50}$ (µM): 5.8

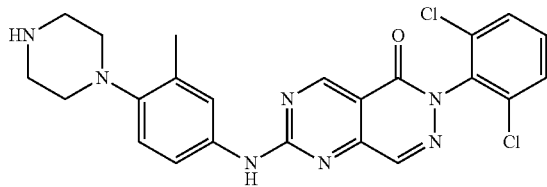

Comparative Example 1 (cf. WO 2013/013031)
Wee1/pCDC2 IC$_{50}$ (nM): 3.8/241
KSol (µM): 107 (avg. 133/80)
hERG IC$_{50}$ (µM): 0.6

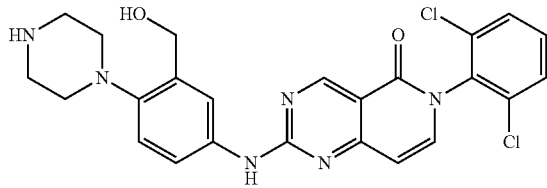

Example 18 of the present invention
Wee1/pCDC2 IC$_{50}$ (nM): 2.7/49
hERG IC$_{50}$ (µM): >11 (4% @ 11 µM)

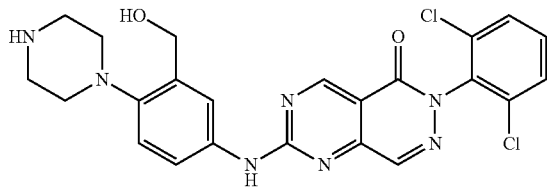

Comparative Example 2 (cf. WO 2013/013031)
Wee1/pCDC2 IC$_{50}$ (nM): 3.9/68
hERG IC$_{50}$ (µM): 4.9

The present inventors have surprisingly found that the compounds of the present invention show an improved or similar kinase-inhibitory effect compared to known compounds or compositions. In particular, the compounds of the present invention preferably show an improved or similar Wee-1 kinase-inhibitory effect compared to known compounds or compositions.

Preferably, the compounds of the present invention have an improved stability in human microsomes e.g. human liver microsomes and/or an improved tolerability and/or reduced hERG inhibition and/or reduced CVS toxicity compared to known compounds or compositions.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

As used in the specification and the appended claims, unless specified to the contrary, the following terms have the meaning indicated:

The term "alkyl group" (alone or in combination with another term(s)) means a straight- or branched-chain saturated hydrocarbyl substituent typically containing 1 to 15 carbon atoms, such as 1 to 10, 1 to 8, 1 to 6, or 1 to 4 carbon atoms. A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

The term "alkenyl group" (alone or in combination with another term(s)) means a straight- or branched-chain hydrocarbyl substituent containing one or more double bonds and typically 2 to 15 carbon atoms; such as 2 to 10, 2 to 8, 2 to 6 or 2 to 4 carbon atoms. Examples of such substituents include ethenyl(vinyl), 2-propenyl, 3-propenyl, 1,4-pentadienyl, 1,4-butadienyl, 1-butenyl, 2-butenyl, 3-butenyl, pentenyl and hexenyl.

The term "alkynyl group" (alone or in combination with another term(s)) means a straight- or branched-chain hydrocarbyl substituent containing one or more triple bonds and typically 2 to 15 carbon atoms; such as 2 to 10, 2 to 8, 2 to 6 or 2 to 4 carbon atoms. Examples of such substituents include ethynyl, 2-propynyl, 3-propynyl, 2-butynyl, and 3-butynyl.

The term "carbocyclyl group" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure. A carbocyclyl may be a single ring structure, which typically contains 3 to 8 ring atoms, more typically 3 to 6 ring atoms, and more typically 5 to 6 ring atoms. Examples of such single-ring carbocyclyls include cyclopropyl(cyclopropanyl), cyclobutyl(cyclobutanyl), cyclopentyl(cyclopentanyl), cyclopentenyl, cyclopentadienyl, cyclohexyl(cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl(dihydroindenyl), anthracenyl, phenanthrenyl, and decalinyl.

The term "cycloalkyl group" (alone or in combination with another term(s)) means a saturated cyclic hydrocarbyl substituent containing 3 to 14 carbon ring atoms. A cycloalkyl may be a single carbon ring, which typically contains 3 to 8 carbon ring atoms and more typically 3 to 6 ring atoms. It is understood that attachment to a cycloalkyl group is via a ring atom of the cycloalkyl group. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl group" (alone or in combination with another term(s)) means an aromatic carbocyclyl containing from 6 to 14 carbon ring atoms, or 3 to 8, 3 to 6 or 5 to 6 carbon ring atoms. An aryl may be monocyclic or polycyclic (i.e., may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, acridinyl, thienyl, indenyl, indanyl, and tetrahydronapthyl.

The term "heterocyclyl group" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms, wherein at least one of the ring atoms is a heteroatom (i.e., oxygen, nitrogen, or sulfur), with the remaining ring atoms being carbon atoms. A heterocyclyl group may, for example, contain one, two, three, four or five heteroatoms. Attachment to the heterocyclyl group may occur either through a carbon atom and/or one or more heteroatoms that are contained in the ring. A heterocyclyl may be a single-ring (monocyclic) or polycyclic ring structure.

A heterocyclyl group may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl(thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl(azinyl), piperidinyl, diazinyl (including pyridazinyl(1,2-diazinyl), pyrimidinyl(1,3-diazinyl), or pyrazinyl(1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl group may alternatively be polycyclic (i.e., may contain more than one ring). Examples of polycyclic heterocyclyl groups include bridged, fused, and spirocyclic heterocyclyl groups. In a spirocyclic heterocyclyl group, one atom is common to two different rings. In a bridged heterocyclyl group, the rings share at least two common non-adjacent atoms. In a fused-ring heterocyclyl group, two or more rings may be fused together, such that two rings share one common bond. Examples of fused ring heterocyclyl groups containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyl groups include benzo-fused heterocyclyl groups, such as indolyl, isoindolyl(isobenzazolyl, pseudoisoindolyl), indoleninyl(pseudoindolyl), isoindazolyl(benzpyrazolyl), benzazinyl (including quinolinyl(1-benzazinyl) or isoquinolinyl(2-benzazinyl)), phthalazinyl, quinoxalinyl, quinazolinyl, benzodiazinyl (including cinnolinyl(1,2-benzodiazinyl) or quinazolinyl(1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl group" (alone or in combination with another term(s)) means a saturated heterocyclyl.

The term "heteroaryl group" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

The term "nitrogen-containing heterocyclyl group" refers to a monocyclic or bicyclic heterocyclyl group containing at least one nitrogen atom, in which each ring comprises from 3 to 7 ring atoms and optionally contains, in addition to the nitrogen atom, zero or one or two or more, the same or different hetero atoms, but preferably zero or one hetero atom selected from the group consisting of an oxygen atom, a nitrogen atom and a sulfur atom; and the heterocyclyl group may be saturated (i.e., "heterocycloalkyl"), partially saturated (i.e., "heterocycloalkenyl"), or completely unsaturated (i.e., "heteroaryl"). The bicyclic heterocyclyl group may have a spiro structure of which the two rings share one and the same ring atom, or may have a bicyclo structure of which the rings share two or more ring atoms. Examples of the nitrogen-containing heterocyclyl group include, for example, a pyrrolyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1, 2,3,5-oxathiadiazolyl group, a piperidinyl group, a piperazinyl group, a dihydropyridyl group, a morpholinyl group, a thiomorpholinyl group, a 2,6-diazaspiro[3.5]nonyl group, a 2,7-diazaspiro[3.5]nonyl group, a 2,7-diazaspiro[4.5]decyl group, or a 2,7-diazabicyclo[3.3.0]octyl group, a 3,6-diazabicyclo[3.3.0]octyl group.

The nitrogen-containing heterocyclyl group can be optionally substituted (a "substituted nitrogen-containing heterocyclyl group") with one or more substituents, which can be the same or different.

The term "amino group" refers to the —NH$_2$ group. The amino group can be optionally substituted (a "substituted amino") with one or more substituents, which can be the same or different. Amino group substituents may be, but are not limited to, an alkyl, alkenyl, alkanoyl, aryl and/or an heterocyclyl group.

The term "amido group" refers to the —C(=O)—NR— group. Attachment may be through the carbon and/or nitrogen atom. For example, the amido group may be attached as a substituent via the carbon atom only, in which case the nitrogen atom has two R groups attached (—C(=O)—NR$_2$). The amido group may be attached by by the nitrogen atom only, in which case the carbon atom has an R group attached (—NR—C(=O)R.

The term "alkoxy group" refers to an alkyl-O group. The alkoxy group can refer to linear, branched, or cyclic, saturated or unsaturated oxo-hydrocarbon chains, including, for example, methoxyl, ethoxyl, propoxyl, isopropoxyl, butoxyl, f-butoxyl and pentoxyl. The alkoxy group can be optionally substituted (a "substituted alkoxy") with one or more alkoxy group substituents.

The term "hydroxyl" refers to an —OH group.

The term "alkanoyl group" (i.e. acyl group) refers to an organic acid group wherein the —OH of the carboxyl group has been replaced with another substituent. Thus, the alkanoyl group can be represented by the formula RC(=O)—, wherein R includes but is not limited to an alkyl, aralkyl, or aryl group, which in turn may be optionally substituted by one or more substituent. Examples of alkanoyl groups include an acetyl group, a propionyl group, a butyryl group, an isobutyryl group, a valeryl group, an isovaleryl group and a pivaloyl group.

The term "sulfonyl group" refers to a sulfonic acid group wherein the wherein the —OH of the sulfonyl group has been replaced with another substituent. For example, the substitutent may be an alkyl group ("an alkylsufonyl group"). An alkylsulfonyl group can be represented by the formula RS(O)$_2$—, wherein R is an alkyl group, optionally substituted by one or more substituent. Examples of alkylsulfonyl groups include a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group and an isohexylsulfonyl group.

The term "sulfinyl group" refers to the bivalent —S(=O) group.

The term "oxo group" refers to the (=O) group, i.e. a substituent oxygen atom connected to another atom by a double bond.

The term "halo group" refers to a group selected from chlorine, fluorine, bromine and iodine.

An alkyl, alkenyl, alkynyl, amino, amido, carbocyclyl (including cycloalkyl, cycloalkenyl and aryl), heterocyclyl (including heterocyloalkyl, heterocyloalkenyl and heteroaryl), sulfonyl, sulfinyl and nitrogen-containing heterocyclyl group can be optionally substituted with one or more substituents, which can be the same or different. A substituent can be attached through a carbon atom and/or a heteroatom in the alkyl, alkenyl, alkynyl, amino, amido, carbocyclyl, heterocyclyl or nitrogen-containing heterocyclyl group. The term "substituent" (or "radical") includes but is not limited to alkyl, substituted alkyl, aralkyl, substituted aralkyl, alkenyl, substituted alkenyl, alkynyl, substituted alkynyl, halo, cyano, amino, amido, alkylamino, arylamino, carbocyclyl, cycloalkyl, substituted cycloalkyl, cycloalkenyl, substituted cycloalkenyl, aryl, substituted aryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl and arylsulfonyl. If a group, for example an alkyl group, is "optionally substituted", it is understood that the group has one or more substituents attached (substituted) or does not have any substituents attached (unsubstituted).

For completeness, it is also noted that certain chemical formulae used herein define delocalized systems. This definition is known in the art as a definition of aromaticity and may indicate the presence of, for example, a mono-, di- or tri-cyclic system that contains (4n+2) electrons where n is an integer. In other words, these systems may display Hückel aromaticity.

In whatever aspect, the compounds of the present invention may possess some aspect of stereochemistry. For example, the compounds may possess chiral centres and/or planes and/or axes of symmetry. As such, the compounds may be provided as single stereoisomers, single diastereomers, mixtures of stereoisomers or as racemic mixtures. Stereoisomers are known in the art to be molecules that have the same molecular formula and sequence of bonded atoms, but which differ in their spatial orientations of their atoms and/or groups.

In addition, the compounds of the present invention may possess tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein. For example, a prodrug may be formed by protecting the —N—H group to which $R^3$ is attached with a hydrolysable group that gives —NH on hydrolysis.

Alternatively or additionally, any —NH group within the compound may be protected as a physiological hydrolyzable amide.

In addition, it will be understood that the elements described herein may be the common isotope or an isotope other than the common isotope. For example, a hydrogen atom may be $^1$H, $^2$H (deuterium) or $^3$H (tritium).

In addition, the compounds of the present invention may be provided in the form of their pharmaceutically acceptable salts or as co-crystals. For example, the compounds may be provided having protonated amine groups.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the Handbook of pharmaceutical salts published by IUPAC.

In addition, the compounds of the present invention may sometimes exist as zwitterions, which are considered as part of the invention.

The present inventors have discovered that the compounds of the present invention are useful in the treatment of medical conditions associated with disordered cell growth, including, but not restricted to, cancer, in particular cancers associated with mutations in the tumour suppressor gene p53.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers.

For example, cancers include adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharangeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, oesophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar.

The compounds of the present invention are also useful in preparing a medicament that is useful in treating the diseases described above, in particular cancer.

The present invention is further directed to a method of inhibiting Wee-1 activity which comprises administering to a mammal in need thereof a pharmaceutically effective amount of the compound of the present invention.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The present invention also includes within its scope the use of the compounds of the present invention in combination with a second or further drug in the treatment of cancer. The second or further drug may be a drug that is already known in the art in the treatment of cancer.

The present invention also includes the use of the compounds of the invention in a regime including the step of radiotherapy. The radiotherapy maybe an ordinary method of treatment by x-ray, Y-ray, neutron, proton or electron beam irradiation. The co-administration of compounds contained in this invention may lead to the potentiation of the radiation therapy, thus classifying them as radio-sensitizers.

In particular, cancers often become resistant to therapy. The development of resistance may be delayed or overcome by the administration of a combination of drugs that includes the compounds of the present invention for example in cancers which are known to be resistant to DNA damaging agents or radiotherapy.

For example, drugs that may be used in combination with the compounds of the present invention may target the same or a similar biological pathway to that targeted by the compounds of the present invention or may act on a different or unrelated pathway.

Depending on the disease to be treated, a variety of combination partners may be co-administered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Bicalutamide) and Luteinisng Hormone Analogues or antagonists.

With regard to combination therapy the compounds of the present invention may be administered separately, sequentially, simultaneously, concurrently or may be chronologically staggered with one or more standard therapeutics such as any of those mentioned above. Preferably, the present invention provides a compound of Formula (I):

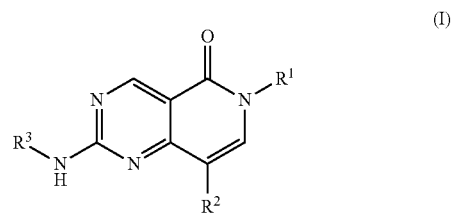

or a pharmaceutically acceptable salt or N-oxide derivative thereof, wherein:
$R^1$ is an optionally substituted aryl or heteroaryl group;
$R^2$ is a hydrogen atom, a halo group, a cyano group, or an optionally substituted aryl, alkyl, alkenyl, alkynyl, cycloalkyl, cycloalkenyl, heterocyclyl, amino or amido group;

R³ is an optionally substituted aryl, alkyl, alkenyl, alkynyl, cycloalkyl, cycloalkenyl or heterocyclyl group.

Preferably, R¹ is a substituted aryl or heteroaryl group.

Preferably, R¹ is a group represented by the formula (a) or (h):

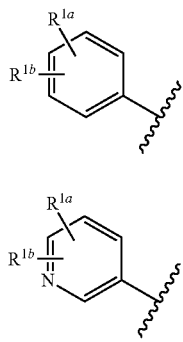

wherein $R^{1a}$ and $R^{1b}$ are each independently selected from the group consisting of a hydrogen atom, a halo group, a hydroxyl group, a cyano group, an amino group, a $C_1$-$C_6$ alkyl group, $C_2$-$C_6$ alkenyl group, a $C_1$-$C_6$ alkoxy group and a $C_1$-$C_6$ alkoxy-$C_1$-$C_6$ alkyl group.

Preferably, R¹ is a group represented by the formula (b) or (i):

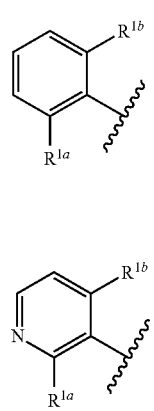

wherein $R^{1a}$ and $R^{1b}$ are each independently selected from the group consisting of a hydrogen atom, a halo group, a hydroxyl group, a cyano group, an amino group, a $C_1$-$C_6$ alkyl group, $C_2$-$C_6$ alkenyl group, a $C_1$-$C_6$ alkoxy group and a $C_1$-$C_6$ alkoxy-$C_1$-$C_6$ alkyl group.

Preferably, in the groups represented by the formulae (a), (h), (b) and/or (i), $R^{1a}$ is a hydrogen atom, a halo group, a cyano group, a methyl group or a methoxy group; and $R^{1b}$ is a halo group. More preferably, $R^{1a}$ is a hydrogen atom or a halo group; and $R^{1b}$ is a halo group. Even more preferably, $R^{1a}$ is a hydrogen atom or a chloro group; and $R^{1b}$ is a chloro group.

Preferably, R¹ is a 2-chlorophenyl group or a 2,6-dichlorophenyl group. Most preferably, is a 2,6-dichlorophenyl group.

Alternately, R¹ is a group represented by the formula (j):

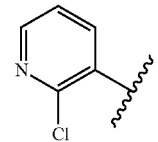

Preferably, R² is a hydrogen atom, a halo group, a cyano group, or an optionally substituted aryl, $C_1$-$C_3$ alkyl or $C_2$-$C_3$ alkynyl, cycloalkyl, cycloalkenyl, heterocyclyl, amino or amido group. It is understood that the term heterocyclyl includes heterocycloalkyl, heterocycloalkenyl and heteroaryl groups. More preferably, R² is a hydrogen atom, a halo group, a methyl group or an optionally substituted amido, $C_2$-$C_3$ alkynyl, phenyl, pyridyl or pyrazolyl group.

Preferably, R² is a hydrogen atom, a methyl group, a bromo group, or a substituted amido or $C_3$-alkynyl group, or an optionally substituted phenyl, pyridyl or pyrazolyl group.

Preferably, R² is an amido group substituted by a methyl group. Alternately, preferably, R² is $C_3$ alkynyl group substituted by a hydroxyl or amino group. More preferably, R² is a hydrogen atom.

Alternately, preferably R² is an optionally substituted phenyl, pyridyl or pyrazolyl group. Preferably, R² is an unsubstituted phenyl or pyridyl group. Alternately, preferably, R² is a phenyl or pyridyl group substituted by a substituted alkyl group, such as a $C_1$-$C_3$-alkyl group substituted by —NR¹⁰R¹¹, wherein R¹⁰ and R¹¹ each independently is a hydrogen atom or a $C_1$-$C_3$ alkyl group, a $C_2$-$C_3$ alkenyl or alkynyl group, or as taken together, they can form an optionally substituted $C_2$-$C_6$ alkyl or alkenyl group (i.e. the nitrogen atom, R¹⁰ and R¹¹ can be part of the same ring). Preferably, —NR¹⁰R¹¹ is —NH₂, —NHMe, —N(Me)₂, —NHEt, —NMeEt, —N(Et)₂ or a piperazinyl or morpholinyl group.

Preferably R³ is an optionally substituted aryl, alkyl, alkenyl, alkynyl, cycloalkyl, cycloalkenyl or heterocyclyl group, wherein the heterocyclyl group contains 1 heteroatom and each of the remaining atoms in the one or more rings is a carbon atom.

Preferably R³ is an optionally substituted aryl, alkyl, alkenyl, alkynyl, cycloalkyl, cycloalkenyl or heterocyclyl group, wherein the heterocyclyl group contains 1 or more heteroatoms selected from the group consisting of nitrogen and oxygen atoms and wherein each of the remaining atoms in the one or more rings is a carbon atom.

Preferably R³ is an optionally substituted aryl, alkyl, alkenyl, alkynyl, cycloalkyl, cycloalkenyl or heterocycloalkyl group.

Preferably R³ is an optionally substituted aryl, alkyl, alkenyl, alkynyl, cycloalkyl or cycloalkenyl group.

Preferably, R³ is a group represented by the formula (c):

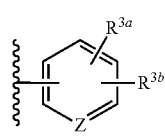

wherein Z is a nitrogen atom or an optionally substituted methine group;

$R^{3a}$ is a hydrogen atom, a halo group, an optionally substituted $C_1$-$C_6$ alkyl group, an optionally substituted $C_2$-$C_6$ alkenyl or alkynyl group, an optionally substituted $C_1$-$C_6$ alkoxy group or is a nitrogen-containing heterocyclyl group optionally substituted with one or more substituents selected from the group consisting of a halo group, an optionally substituted $C_1$-$C_6$ alkyl group, an optionally substituted $C_2$-$C_6$ alkenyl or alkynyl group, one or two or more oxo groups and an optionally substituted amino group;

$R^{3b}$ is a hydrogen atom, a halo group, a cyano group, an optionally substituted $C_1$-$C_6$ alkyl group, an optionally substituted $C_2$-$C_6$ alkenyl or alkynyl group, or an optionally substituted $C_1$-$C_6$ alkoxy group;

or, when $R^{3a}$ and $R^{3b}$ exist on adjacent ring atoms of the group of the formula (d):

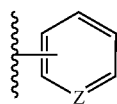

(d)

$R^{3a}$ and $R^{3b}$ and the ring atoms to which they are attached can optionally form, as taken together, a $C_3$-$C_7$ alkyl or alkenyl group, in which one or two methylene groups constituting the $C_3$-$C_7$ alkyl or alkenyl group can be optionally each independently replaced by an oxygen atom or a group of —N($R^{4a}$)—, and the $C_3$-$C_7$ alkyl or alkenyl group can be optionally substituted with one or more substituents selected from the group consisting of a halo group, a $C_1$-$C_6$ alkyl group and a $C_2$-$C_6$ alkenyl or alkynyl group;

or $R^{3a}$ and $R^{3b}$ and the ring atoms to which they are attached can optionally form, as taken together, a spiro ring or a bicyclo ring to be formed of a 5-membered to 7-membered aliphatic ring and any other 3-membered to 7-membered aliphatic ring, in which one or two or more methylene groups constituting the spiro ring or the bicyclo ring can be optionally each independently replaced by an oxygen atom, a sulfur atom, a sulfinyl group, a sulfonyl group, an oxo group or a group of —N($R^{4b}$)—, and the spiro ring or the bicyclo ring can be optionally each independently substituted with a substituent selected from the group consisting of a halo group, a hydroxyl group, a $C_1$-$C_6$ alkyl group and a $C_2$-$C_6$ alkenyl or alkynyl group; and $R^{4a}$ and $R^{4b}$ are each independently a hydrogen atom, a $C_1$-$C_6$ alkyl group or $C_2$-$C_6$ alkenyl or alkynyl group optionally substituted with a substituent selected from the group consisting of a halo group, a hydroxyl group, a cyano group, an oxo group, a $C_1$-$C_6$ alkyl group, a $C_2$-$C_6$ alkenyl or alkynyl group, a $C_1$-$C_6$ alkoxy group, an amino group, a substituted amino group and a nitrogen-containing heterocyclyl group.

Preferably, Z is an optionally substituted methine group.

Preferably, $R^3$ is a group represented by the formula (e):

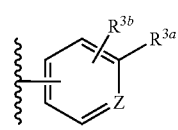

(e)

wherein $R^{3a}$ is a hydrogen atom, a halo group, a $C_1$-$C_6$ alkyl group, a $C_2$-$C_6$ alkenyl or alkynyl group, an optionally substituted $C_1$-$C_6$ alkoxy group, or is a nitrogen-containing heterocyclyl group optionally substituted with one or more substituents selected from the group consisting of a halo group, a $C_1$-$C_6$ alkyl group, a $C_2$-$C_6$ alkenyl or alkynyl group, one or two or more oxo groups and a group of -$Q^1$-N($R^{4c}$)$R^{4d}$;

$R^{3b}$ is a hydrogen atom, a halo group, an optionally substituted $C_1$-$C_6$ alkyl group, an optionally substituted $C_2$-$C_6$ alkenyl or alkynyl group, an optionally substituted $C_1$-$C_6$ alkoxy group, or a cyano group;

$R^{4c}$ and $R^{4d}$ each independently is a hydrogen atom or a $C_1$-$C_6$ alkyl group, a $C_2$-$C_6$ alkenyl or alkynyl group, or as taken together, they can form an optionally substituted $C_2$-$C_6$ alkyl or alkenyl group; and $Q^1$ is a single bond, a $C_1$-$C_3$ alkyl group or a $C_2$-$C_3$ alkenyl or alkynyl group.

Preferably, in the groups represented by the formula (c) and/or (e), $R^{3a}$ is a substituted $C_1$-$C_6$ alkoxy group, a substituted $C_1$-$C_3$ alkyl group or a nitrogen-containing heterocyclyl group optionally substituted with a substituent selected from the group consisting of two oxo groups and an optionally substituted $C_1$-$C_3$ alkyl group; and $R^{3b}$ is a hydrogen atom, a halo group, a methoxyl group or a $C_1$-$C_2$ alkyl group optionally substituted with a substituent selected from the group consisting of a hydroxyl group and an amino group.

Preferably, in the groups represented by the formula (c) and/or (e), $R^{3a}$ is a substituted $C_1$-$C_2$ alkoxy group, a substituted $C_1$-$C_2$ alkyl group or a nitrogen-containing heterocyclyl group with a substituent selected from the group consisting of two oxo groups and an optionally substituted $C_1$-$C_3$ alkyl group; and $R^{3b}$ is a hydrogen atom, a halo group, a methoxyl group or a $C_1$-$C_2$ alkyl group optionally substituted with a substituent selected from the group consisting of a hydroxyl group and an amino group.

Preferably, when $R^{3a}$ is a substituted $C_1$-$C_6$ alkoxy group, preferably a substituted $C_1$-$C_2$ alkoxy group, the substituent is an amino group substituted by one or two methyl groups.

Preferably, when $R^{3a}$ is a substituted $C_1$-$C_3$ alkyl group, preferably a substituted $C_1$-$C_2$ alkyl group, the substituent is a hydroxyl group or an amino group substituted by one or two methyl groups.

Preferably, $R^{3a}$ is an unsubstituted nitrogen-containing heterocyclyl group.

Alternately, $R^{3a}$ is preferably a nitrogen-containing heterocyclyl group substituted with a substituent selected from the group consisting of two oxo groups and an optionally substituted $C_1$-$C_3$ alkyl group. Preferably, when $R^{3a}$ is a nitrogen-containing heterocyclyl group substituted by an optionally substituted $C_1$-$C_3$ alkyl group, the optionally substituted $C_1$-$C_3$ alkyl group is selected from the group consisting of an ethyl group substituted by an oxo group, a methyl group, an ethyl group, and an isopropyl group. Preferably, when the nitrogen-containing heterocyclyl group is substituted with two oxo groups, the nitrogen-containing heterocyclyl group contains one sulfur atom and the two oxo groups are both attached by respective double bonds to the sulfur atom.

Preferably, R³ is a group represented by the formula (f):

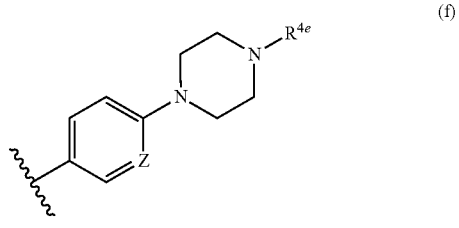

(f)

wherein R$^{4e}$ is selected from the group consisting of a hydrogen atom, an optionally substituted alkanoyl group, an optionally substituted C$_1$-C$_6$ alkyl group and a C$_2$-C$_6$ alkenyl group. More preferably, R$^{4e}$ is selected from the group consisting of a hydrogen atom and an optionally substituted C$_1$-C$_6$ alkyl group. Preferably, R$^{4e}$ is selected from the group consisting of a hydrogen atom and an optionally substituted C$_1$-C$_3$ alkyl group. Preferably, when R$^{4e}$ is an optionally substituted C$_1$-C$_3$ alkyl group, the optionally substituted C$_1$-C$_3$ alkyl group is selected from the group consisting of an ethyl group substituted by an oxo group, an ethyl group substituted by an oxo and a hydroxyl group (i.e. —CH$_2$—C(═O)OH), a methyl group, an ethyl group, and an isopropyl group. Preferably, the optionally substituted C$_1$-C$_3$ alkyl group is a methyl group. Alternately, preferably, the the optionally substituted C$_1$-C$_3$ alkyl group is an ethyl group substituted by an oxo and a hydroxyl group (i.e. —CH$_2$—C(═O)OH).

Preferably, Z is an optionally substituted methine group.

Alternately, preferably R³ is a group represented by the formula (g):

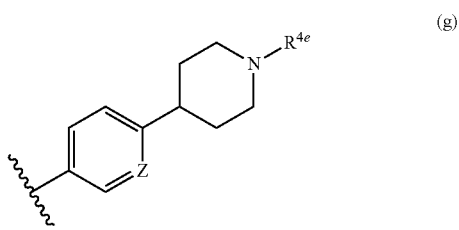

(g)

wherein R$^{4e}$ is selected from the group consisting of a hydrogen atom, an optionally substituted alkanoyl group, an optionally substituted C$_1$-C$_6$ alkyl group and a C$_2$-C$_6$ alkenyl group. Preferably, R$^{4e}$ is selected from the group consisting of a hydrogen atom and an optionally substituted C$_1$-C$_3$ alkyl group. Preferably, when R$^{4e}$ is an optionally substituted C$_1$-C$_3$ alkyl group, the optionally substituted C$_1$-C$_3$ alkyl group is a methyl group.

Alternately, preferably R³ is a group represented by the formula (k):

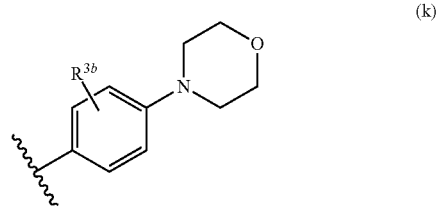

(k)

wherein R$^{3b}$ is a hydrogen atom, a halo group, a cyano group, an optionally substituted C$_1$-C$_6$ alkyl group, an optionally substituted C$_2$-C$_6$ alkenyl or alkynyl group, or an optionally substituted C$_1$-C$_6$ alkoxy group. Preferably, R$^{3b}$ is a hydrogen atom or a methyl group substituted with —NHMe.

Alternately, preferably R³ is a group represented by the formula (m):

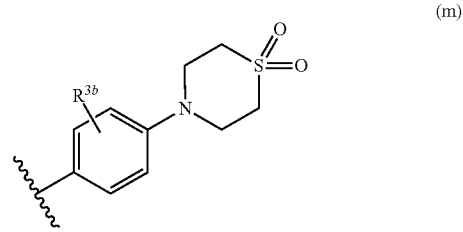

(m)

wherein R$^{3b}$ is a hydrogen atom, a halo group, a cyano group, an optionally substituted C$_1$-C$_6$ alkyl group, an optionally substituted C$_2$-C$_6$ alkenyl or alkynyl group, or an optionally substituted C$_1$-C$_6$ alkoxy group. Preferably, R$^{3b}$ is a hydrogen atom or a methyl group substituted with —NHMe.

Preferably, in the compound of Formula (I), R¹ is an optionally substituted aryl group; R² is a hydrogen atom, a C$_1$-C$_2$ alkyl group, a halo group, a substituted amido or C$_3$-alkynyl group, or an optionally substituted phenyl, pyridyl or pyrazolyl group; and R³ is an optionally substituted aryl group.

More preferably, R¹ is a group represented by the formula (a) or (h) as defined above and/or R² is a hydrogen atom, a methyl group, a bromo group, a substituted amido or C$_3$-alkynyl group, or an optionally substituted phenyl, pyridyl or pyrazolyl group and/or R³ is a group represented by the formula (c) as defined above.

Even more preferably, R¹ is a group represented by the formula (b) or (i) as defined above and/or R² is a hydrogen atom, a methyl group, a bromo group, a substituted amido or C$_3$-alkynyl group, or an optionally substituted phenyl or pyridyl group and/or R³ is a group represented by the formula (e) as defined above.

More preferably still, R¹ is a 2-chlorophenyl group or a 2,6-dichlorophenyl group, R² is a hydrogen atom, a methyl group, a substituted C$_3$-alkynyl group or an optionally substituted phenyl or pyridyl group and/or R³ is a group represented by the formula (f), (g), (k) or (m) as defined above.

Most preferably, R¹ is a 2,6-dichlorophenyl group and/or R² is a hydrogen atom and/or R³ is a group represented by the formula (f) or (g) as defined above.

Preferably, the compound of formula (I) is selected from the following:

(1) 6-(2,6-Dichlorophenyl)-2-((4-(piperazin-1-yl)phenyl)amino)pyrido[4,3-d]pyrimidin-5(6H)-one;
(2) 6-(2,6-Dichlorophenyl)-8-methyl-2-((4-(piperazin-1-yl)phenyl)amino)pyrido[4,3-d]pyrimidin-5(6H)-one;
(3) 6-(2-Chloropyridin-3-yl)-2-((4-(piperazin-1-yl)phenyl)amino)pyrido[4,3-d]pyrimidin-5(6H)-one;
(4) 6-(2,6-Dichlorophenyl)-2-((4-(2-(diethylamino)ethoxy)phenyl)amino)pyrido[4,3-d]pyrimidin-5(6H)-one;
(5) 2-((4-(4-Acetylpiperazin-1-yl)phenyl)amino)-6-(2,6-dichlorophenyl)pyrido[4,3-d]pyrimidin-5(6H)-one;
(6) 6-(2,6-Dichlorophenyl)-2-((4-(1,1-dioxidothiomorpholino)phenyl)amino)pyrido[4,3-d]pyrimidin-5(6H)-one;
(7) 6-(2,6-Dichlorophenyl)-2-((3-methyl-4-(piperazin-1-yl)phenyl)amino)pyrido[4,3-d]pyrimidin-5(6H)-one;

(8) 6-(2,6-Dichlorophenyl)-2-((3-(hydroxymethyl)-4-(4-methylpiperazin-1-yl)phenyl)amino)pyrido[4,3-d]pyrimidin-5(6H)-one;
(9) 8-Bromo-6-(2,6-dichlorophenyl)-2-((4-(piperazin-1-yl)phenyl)amino)pyrido[4,3-d]pyrimidin-5(6H)-one;
(10) 6-(2,6-Dichlorophenyl)-2-((4-(1-methylpiperidin-4-yl)phenyl)amino)pyrido[4,3-d]pyrimidin-5(6H)-one;
(11) 6-(2,6-Dichlorophenyl)-2-((4-(2-(dimethylamino)ethyl)phenyl)amino)pyrido[4,3-d]pyrimidin-5(6H)-one;
(12) 6-(2,6-Dichlorophenyl)-2-((3-methoxy-4-(4-methylpiperazin-1-yl)phenyl)amino)pyrido[4,3-d]pyrimidin-5(6H)-one;
(13) 6-(2,6-Dichlorophenyl)-2-((3-methoxy-4-(piperazin-1-yl)phenyl)amino)pyrido[4,3-d]pyrimidin-5(6H)-one;
(14) 6-(2,6-Dichlorophenyl)-8-(3-hydroxyprop-1-yn-1-yl)-2-((3-methyl-4-(piperazin-1-yl)phenyl)amino)pyrido[4,3-d]pyrimidin-5(6H)-one;
(15) 6-(2,6-Dichlorophenyl)-2-((4-(4-methylpiperazin-1-yl)phenyl)amino)pyrido[4,3-d]pyrimidin-5(6H)-one;
(16) 6-(2,6-Dichlorophenyl)-2-((4-(2-(methylamino)ethoxy)phenyl)amino)pyrido[4,3-d]pyrimidin-5(6H)-one;
(17) 6-(2,6-Dichlorophenyl)-2-((4-(4-isopropylpiperazin-1-yl)phenyl)amino)pyrido[4,3-d]pyrimidin-5(6H)-one;
(18) 6-(2,6-Dichlorophenyl)-2-((3-(hydroxymethyl)-4-(piperazin-1-yl)phenyl)amino)pyrido[4,3-d]pyrimidin-5(6H)-one;
(19) 6-(2,6-Dichlorophenyl)-2-((4-morpholinophenyl)amino)pyrido[4,3-d]pyrimidin-5(6H)-one;
(20) 6-(2,6-Dichlorophenyl)-2-((3-((methylamino)methyl)-4-morpholinophenyl)amino)pyrido[4,3-d]pyrimidin-5(6H)-one;
(21) 6-(2,6-Dichlorophenyl)-2-((4-(4-(2-hydroxyethyl)piperazin-1-yl)phenyl)amino)pyrido[4,3-d]pyrimidin-5(6H)-one;
(22) 8-(3-Aminoprop-1-yn-1-yl)-6-(2,6-dichlorophenyl)-2-((4-morpholinophenyl)amino)pyrido[4,3-d]pyrimidin-5(6H)-one;
(23) 6-(2,6-Dichlorophenyl)-2-((4-(piperazin-1-yl)phenyl)amino)-8-(pyridin-3-yl)pyrido[4,3-d]pyrimidin-5(6H)-one;
(24) 6-(2-Chlorophenyl)-2-((3-methyl-4-(piperazin-1-yl)phenyl)amino)pyrido[4,3-d]pyrimidin-5(6H)-one;
(25) 2-((3-(Aminomethyl)phenyl)amino)-6-(2,6-dichlorophenyl)pyrido[4,3-d]pyrimidin-5(6H)-one;
(26) 6-(2,6-Dichlorophenyl)-2-((3-(4-methylpiperazin-1-yl)phenyl)amino)pyrido[4,3-d]pyrimidin-5(6H)-one;
(27) 2-((3-Chloro-4-(piperazin-1-yl)phenyl)amino)-6-(2,6-dichlorophenyl)pyrido[4,3-d]pyrimidin-5(6H)-one;
(28) N-(6-(2,6-Dichlorophenyl)-5-oxo-2-((4-(piperazin-1-yl)phenyl)amino)-5,6-dihydropyrido[4,3-d]pyrimidin-8-yl)acetamide;
(29) 6-(2,6-Dichlorophenyl)-2-((3-fluoro-4-(piperazin-1-yl)phenyl)amino)pyrido[4,3-d]pyramidin-5(6H)-one;
(30) 6-(2,6-Dichlorophenyl)-2-((3,5-difluoro-4-(piperazin-1-yl)phenyl)amino)pyrido[4,3-d]pyrimidin-5(6H)-one;
(31) 6-(2,6-Dichlorophenyl)-2-((6-(4-methylpiperazin-1-yl)pyridin-3-yl)amino)pyrido[4,3-d]pyrimidin-5(6H)-one;
(32) 6-(2,6-Dichlorophenyl)-2-((4-(4-methylpiperazine-1-carbonyl)phenyl)amino)pyrido[4,3-d]pyrimidin-5(6H)-one; and
(33) 2-(4-(4-((6-(2,6-Dichlorophenyl)-5-oxo-5,6-dihydropyrido[4,3-d]pyrimidin-2-yl)amino)phenyl)piperazin-1-yl)acetic acid.

Preferably, there is provided the compound of formula (I), or a pharmaceutically acceptable salt or N-oxide derivative thereof, and at least one pharmaceutically acceptable excipient.

Suitable pharmaceutically acceptable excipients would be known by the person skilled in the art, for example, fats, water, physiological saline, alcohol (e.g., ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

Preferably, there is provided a pharmaceutical composition comprising the compound of formula (I), or a pharmaceutically acceptable salt or N-oxide derivative thereof, and at least one pharmaceutically acceptable excipient.

Preferably, there is provided a pharmaceutical composition comprising the compound of formula (I) comprising one or more further pharmaceutically active agents.

Preferably, there is provided the compound of formula (I), or a pharmaceutically acceptable salt or N-oxide derivative thereof, or a pharmaceutical composition comprising the compound of formula (I) for use in therapy.

Preferably, there is provided the compound of formula (I) for use as a medicament.

Preferably, there is provided the compound of formula (I) for use in treating or preventing cancer.

Preferably, there is provided the compound of formula (I), or a pharmaceutically acceptable salt or N-oxide derivative thereof, or a pharmaceutical composition comprising the compound of formula (I) for use as a medicament and/or for use in treating or preventing cancer.

Preferably, there is provided the use of the compound of formula (I) for the manufacture of a medicament for treating or preventing cancer.

Preferably, there is provided a method of treating or preventing cancer in a human or animal patient comprising administering to a patient in need thereof an effective amount of a compound of formula {I} or a pharmaceutical composition comprising formula (I).

Preferably, the compounds of the present invention have an $IC_{50}$ value for Wee-1 kinase of about 1 nM to about 1,000 nM, more preferably from about 1 nM to about 500 nM, or from about 1 nM to about 300 nM, or from about 1 nM to about 100 nM, or from about 1 nM to about 50 nM, or from about 1 nM to about 30 nM, or from about 1 nM to about 15 nM, or from about 1 nM to about 10 nM, most preferably less than 10 nM. A method for determining the $IC_{50}$ value of a compound for Wee-1 kinase is described below (see examples).

When introducing elements of the present disclosure or the preferred embodiments(s) thereof, the articles "a", "an", "the" and "said" are intended to mean that there are one or more of the elements. The terms "comprising", "including"

and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The following non-limiting examples further illustrate the present invention.

EXAMPLES

The present invention will now be described in relation to several examples.

Examples 1 to 33 were synthesised according to the methods described subsequently. $IC_{50}$ values were determined as described below and are represented in the following table.

TABLE 1

| Example Number | Wee-1 $IC_{50}$ activity | HT29 pCDC2 activity | HLM activity | hERG activity |
|---|---|---|---|---|
| 1 | ** | * | *** | |
| 2 | *** | ** | *** | *** |
| 3 | * | | *** | |
| 4 | ** | ** | ** | |
| 5 | ** | ** | *** | |
| 6 | ** | ** | ** | |
| 7 | *** | *** | *** | ** |
| 8 | *** | ** | *** | * |
| 9 | *** | ** | *** | |
| 10 | *** | ** | *** | ** |
| 11 | ** | ** | ** | ** |
| 12 | ** | *** | ** | ** |
| 13 | *** | *** | *** | *** |
| 14 | *** | *** | *** | |
| 15 | ** | ** | ** | ** |
| 16 | ** | ** | *** | *** |
| 17 | ** | ** | ** | ** |
| 18 | *** | *** | *** | *** |
| 19 | ** | * | ** | *** |
| 20 | *** | *** | *** | *** |
| 21 | *** | *** | ** | |
| 22 | *** | *** | ** | |
| 23 | *** | *** | ** | |
| 24 | *** | ** | *** | |
| 25 | ** | * | ** | |
| 26 | ** | * | ** | |
| 27 | *** | ** | *** | |
| 28 | * | | | |
| 29 | *** | *** | *** | |
| 30 | ** | * | *** | |
| 31 | ** | ** | ** | |
| 32 | ** | ** | | |
| 33 | ** | | | |

For representative examples in Table 1, Wee-1, HT29 pCDC2, HLM and hERG activities are classified as the following:

| | *** | ** | * |
|---|---|---|---|
| Wee-1 $IC_{50}$ [nM] | ≤10 | 10-200 | ≥200 |
| pCDC2 [nM] | ≤100 | 100-1000 | ≥1000 |
| HLM CLint [μL/min/mg] | ≤20 | >20 | |
| hERG $IC_{50}$ [μM] | ≥10 | 1->10 | ≤1 |

Compounds were tested for inhibition of the human ether a go-go related gene (hERG) K⁺ channel using IonWorks patch clamp electrophysiology at Essen BioScience. 8-Point concentration-response curves of the effect of compound on hERG current as a percentage of pre-compound signal were generated using 3-fold serial dilutions from 11 μM and results are reported as IC50 in μM.

All of example compounds 1 to 33 also exhibit an improved stability in human liver microsomes and have a CLint of <40.

Compounds of the present invention have good stability in human and/or rat hepatocyte incubations. In particular, representative examples 7, 8, 13, 18, 20 have CLint of <20 μL/min/$10^6$ cells in a human hepatocyte assay and/or <40 μL/min/$10^6$ cells in a rat hepatocyte assay.

Compounds of the present invention are orally bioavailable. In particular, representative examples 7, 13 and 20 have oral bioavailability of >25% in rat.

Compounds of the present invention have no time dependent CYP inhibition. In particular, representative examples 13 and 20 show no time dependent inhibition of CYP3A4, CYP1A2, CYP2C9, CYP2C19 or CYP2D6 (<2 fold shift in IC50 following a 30 min pre incubation ±NADPH relative to direct inhibition IC50 with no pre-incubation).

Experimental Section

Abbreviations aq: aqueous; dba: dibenzylideneacetone; DCM: dichloromethane; DIPEA: diisopropylethylamine; DMF: N,N-dimethylformamide; DMSO: dimethylsulfoxide; dppf: 1,1'-bis (diphenylphosphino)ferrocene; EtOAc: ethyl acetate; ESI: electrospray ionisation; h: hour; HPLC: high pressure liquid chromatography; LC: liquid chromatography; LCMS: liquid chromatography mass spectrometry; M: molar; m/z: mass-to-charge ratio; mCPBA: 3-chloroperbenzoic acid; MeOH: methanol; min: minutes; MS: mass spectrometry; NBS: N-bromosuccinimide; NMR: nuclear magnetic resonance; $R_T$: retention time; RT: room temperature; SM: starting material; TFA: trifluoroacetic acid; THF: tetrahydrofuran; Xantphos: 4,5-bis(diphenylphosphino)-9,9-dimethylxanthene.

General Experimental Conditions

Solvents and Reagents

Common organic solvents that were used in reactions (e.g. THF, DMF, DCM, and methanol) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Microwave Synthesis

Unless quoted otherwise, microwave experiments were carried out using a CEM Discover™/Explorer24™ system controlled by Synergy 1.5 software. In other cases a Biotage Initiator™ Eight was used. Both machines give good reproducibility and control at temperature ranges from 60-250° C. and pressures of up to maximum of 20 bar.

Flash Chromatography

Purification of compounds by flash chromatography was achieved using a Biotage Isolera Four system. Unless otherwise stated, Biotage KP-Sil SNAP cartridge columns (10-340 g) were used along with the stated solvent system and an appropriate solvent gradient depending on compound polarity. In the case of more polar and basic compounds, Biotage KP-NH SNAP cartridge columns (11 g) were used.

NMR Spectroscopy $^1$H NMR spectra were recorded at ambient temperature using a Bruker Avance (500 MHz) spectrometer. All chemical shifts (δ) are expressed in ppm. Residual solvent signals were used as an internal standard and the characteristic solvent peaks were corrected to the reference data outlined in J. Org. Chem., 1997, 62, p 7512-7515; in other cases, NMR solvents contained tetramethylsilane, which was used as an internal standard.

High Pressure Liquid Chromatography

Liquid Chromatography Mass Spectrometry (LCMS) experiments to determine retention times (RT) and associated mass ions were performed using one of the following methods:

Method A: The system consists of an Agilent Technologies 6140 single quadrupole mass spectrometer linked to an Agilent Technologies 1290 Infinity LC system with UV diode array detector and autosampler. The spectrometer consists of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Method B: The system consisted of a ThermoFinnigan LCQ Advantage Mass Spectrometer with Surveyor LC system and 200 position autosampler. The LC system was coupled to an inline Surveyor DAD detector and ESI source operating in positive and negative ion mode. LCMS experiments were performed on each sample submitted using the following conditions: LC Column: Luna 3 micron C18 50×2 mm. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 0.6 | 95 | 5 |
| 7.00 | 0.6 | 5 | 95 |
| 8.00 | 0.6 | 5 | 95 |
| 8.20 | 0.6 | 95 | 5 |
| 11.00 | 0.6 | 95 | 5 |

Preparative High Pressure Liquid Chromatography

The system consisted of an Agilent Technologies 6120 single quadrupole mass spectrometer linked to an Agilent Technologies 1200 Preparative LC system with Multiple Wavelength detector and autosampler. The mass spectrometer used a multimode ionization source (electrospray and atmospheric pressure chemical ionizations) operating in positive and negative ion mode. Fraction collection was mass-triggered (multimode positive and negative ion). Purification experiments, unless otherwise stated, were performed under basic conditions at an appropriate solvent gradient that was typically determined by the retention time found using HPLC Method A. In cases were the basic conditions were unsuccessful, acidic conditions were employed.

Basic Conditions: LC Column: Waters XBridge™ Prep C18 5 μm OBD™ 19×50 mm column at RT. Mobile phase: A) 0.1% (v/v) ammonium hydroxide in water; B) 0.1% (v/v) ammonium hydroxide in 95:5, acetonitrile/water. Total experiment time was ca. 10 min and an example method is given:

| Gradient Time (min) | Flow (mL/min) | % A | % B |
|---|---|---|---|
| 0.00 | 20.0 | 50 | 50 |
| 3.00 | 20.0 | 12 | 88 |
| 5.00 | 20.0 | 12 | 88 |
| 7.00 | 20.0 | 0 | 100 |
| 8.0 | 20.0 | 0 | 100 |
| 8.20 | 20.0 | 50 | 50 |

Acidic Conditions: LC Column: Waters XBridge™ Prep C18 5 μm OBD™ 19×50 mm column at RT. Mobile phase: A) Water 0.1% (v/v) formic acid in water; B) 0.1% (v/v) formic acid in 95:5, acetonitrile/water. Total experiment time was ca. 10 min and an example method is given:

| Gradient Time (min) | Flow (mL/min) | % A | % B |
|---|---|---|---|
| 0.00 | 20.0 | 95 | 5 |
| 7.00 | 20.0 | 0 | 100 |
| 9.00 | 20.0 | 0 | 100 |
| 9.20 | 20.0 | 95 | 5 |

The pure fractions were combined and concentrated using a Genevac EZ-2 Elite, unless stated otherwise.

Nomenclature

Unless otherwise indicated, the nomenclature of structures was determined using the 'Convert Structure to Name' function of ChemBioDraw Ultra 12.0.2 (CambridgeSoft/PerkinElmer).

Example 1

6-(2,6-Dichlorophenyl)-2-((4-(piperazin-1-yl)phenyl)amino)pyrido[4,3-d]pyrimidin-5(6H)-one

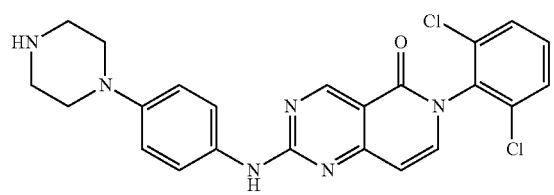 [SMILES: O=c1c2cnc(Nc3ccc(N4CCNCC4)cc3)nc2ccn1-c1c(Cl)cccc1Cl]

Step 1: N-(2,6-Dichlorophenyl)-4-methyl-2-(methylthio)pyrimidine-5-carboxamide: Phosphorus trichloride (2.37 mL, 27.1 mmol) was added to a stirred solution of 4-methyl-2-(methylthio)pyrimidine-5-carboxylic acid (5.00 g, 27.1 mmol) [commercially available] and 2,6-dichloroaniline (4.40 g, 27.1 mmol) in chlorobenzene (100 mL) at 135° C. under nitrogen. After 3 h, the solvents were removed in vacuo, the remaining residue was partitioned between DCM and 2M sodium carbonate (aq) solution, separated, extracted (DCM×2), and dried (Phase Separator), and the solvents were removed in vacuo to give the title compound (6.86 g, 77%) as a pale yellow solid. LCMS (Method A): RT=1.14 min, m/z=328, 330 [M+H]⁺.

Step 2: 6-(2,6-Dichlorophenyl)-2-(methylthio)pyrido[4,3-d]pyrimidin-5(6H)-one DMF-DMA (2.49 mL, 18.6 mmol) was added to a stirred solution of N-(2,6-dichlorophenyl)-4-methyl-2-(methylthio)pyrimidine-5-carboxamide (5.08 g, 15.5 mmol) in DMF (50 mL) at RT under nitrogen. The reaction mixture was heated to 100° C. After 2 h, due to incomplete reaction, further DMF-DMA (1.0 mL, 7.74 mmol) was added. After a further 2 h, due to incomplete reaction, further DMF-DMA (0.5 mL, 3.87 mmol) was added. After a further 1 h, the reaction mixture was cooled to RT and was partitioned between diethyl ether and 1:1 water/brine, separated, extracted (diethyl ether×2), dried (Phase Separator), the solvents were removed in vacuo, and the remaining residue was purified by flash chromatography (0-100%, EtOAc in cyclohexane) to give the title compound (2.38 g, 46%) as a pale yellow solid. LCMS (Method A): RT=1.29 min, m/z=338, 340 [M+H]⁺.

Step 3: tert-Butyl 4-(4-((6-(2,6-dichlorophenyl)-5-oxo-5,6-dihydropyrido[4,3-d]pyrimidin-2-yl)amino)phenyl)piperazine-1-carboxylate: mCPBA (<77% pure) (23.0 mg, assumed 0.102 mmol) in DCM (0.5 mL) was added to a stirred solution of 6-(2,6-dichlorophenyl)-2-(methylthio)pyrido[4,3-d]pyrimidin-5(6H)-one (30.0 mg, 0.089 mmol) in toluene (1.5 mL) at RT under nitrogen. After 15 min, DIPEA (0.046 mL, 0.266 mmol) and tert-butyl 4-(4-aminophenyl)piperazine-1-carboxylate (27.1 mg, 0.098 mmol) [commercially available] were added, successively and the temperature was increased to 60° C. After 16 h, the reaction mixture was allowed to cool to RT, and was loaded directly onto a KP-NH column and purified by flash chromatography (0-100%, EtOAc in cyclohexane). The pure fractions were concentrated to give the title compound (30.5 mg, 61%) as a yellow solid. LCMS (Method A): R$_T$=1.50 min, m/z=567, 569 [M+H]⁺.

Step 4: 6-(2,6-Dichlorophenyl)-2-((4-(piperazin-1-yl)phenyl)amino)pyrido[4,3-d]pyrimidin-5(6H)-one: TFA (2.0 mL, 26.0 mmol) was added to a stirred solution of tert-butyl 4-(4-((6-(2,6-dichlorophenyl)-5-oxo-5,6-dihydropyrido[4,3-d]pyrimidin-2-yl)amino)phenyl)piperazine-1-carboxylate (30.5 mg, 0.054 mmol) in DCM (2.0 mL) at RT under nitrogen. After 30 min, the solvents were removed in vacuo and the remaining residue was partitioned between saturated sodium bicarbonate (aq) solution and DCM, separated, extracted (DCM×2), and dried (Phase Separator). The solvents were removed in vacuo to give the title compound (24.9 mg, 98%) as a yellow solid. LCMS (Method A): R$_T$=0.82 min, m/z=467, 469 [M+H]⁺. ¹H NMR (500 MHz, methanol-d4): δ 9.19 (s, 1H), 7.69-7.60 (m, 4H), 7.52 (dd, 1H), 7.47 (d, 1H), 7.01 (d, 2H), 6.60 (d, 1H), 3.17-3.12 (m, 4H), 3.03-2.98 (m, 4H).

Example 2

6-(2,6-Dichlorophenyl)-8-methyl-2-((4-(piperazin-1-yl)phenyl)amino)pyrido[4,3-d]pyrimidin-5(6H)-one

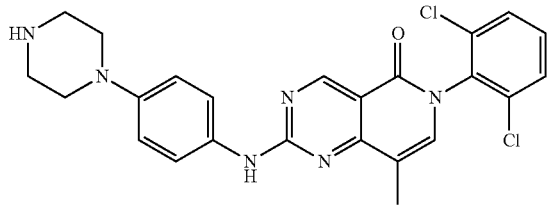 [SMILES: Cc1cn(-c2c(Cl)cccc2Cl)c(=O)c2cnc(Nc3ccc(N4CCNCC4)cc3)nc12]

Step 1: 8-Bromo-6-(2,6-dichlorophenyl)-2-(methylthio)pyrido[4,3-d]pyrimidin-5(6H)-one: NBS (5.3 mg, 0.030 mmol) was added to a stirred solution of 6-(2,6-dichlorophenyl)-2-(methylthio)pyrido[4,3-d]pyrimidin-5(6H)-one (10.0 mg, 0.030 mmol) in acetonitrile (1.0 mL) at 80° C. under nitrogen in a 4 mL sealed vial. After 16 h, LCMS analysis showed a 2:1 mixture of product/SM. Further NBS (2.6 mg, 0.5 eq) was added. After a further 1 h, the reaction mixture was quenched with 10% sodium bisulfite and partitioned with DCM, separated, extracted (DCM×2), dried (Phase Separator), the solvents were removed in vacuo, and the remaining residue was purified by flash chromatography (0-100%, EtOAc in cyclohexane) to give the title compound (9.5 mg, 77%) as a pale yellow solid. LCMS (Method A): R$_T$=1.47 min, m/z=418 [M+H]⁺. ¹H NMR (500 MHz, CDCl₃): δ 9.36 (s, 1H), 7.56 (s, 1H), 7.54-7.50 (m, 2H), 7.42 (dd, 1H), 2.73 (s, 3H).

Step 2: 6-(2,6-Dichlorophenyl)-8-methyl-2-(methylthio)pyrido[4,3-d]pyrimidin-5(6H)-one: PdCl₂(dppf).DCM (0.9 mg, 1.14 μmol) was added to a pre-degassed solution of 8-bromo-6-(2,6-dichlorophenyl)-2-(methylthio)pyrido[4,3-d]pyrimidin-5(6H)-one (9.5 mg, 0.023 mmol), 2,4,6-trimethyl-1,3,5,2,4,6-trioxatriborinane (6.4 μl, 0.046 mmol) and potassium carbonate (9.4 mg, 0.068 mmol) in 1,4-dioxane (1.0 mL) in a 4 mL vial. The vessel was sealed and heated to 100° C. After 16 h, the solvents were removed in vacuo and the remaining residue was purified by flash chromatography (0-100%, EtOAc in cyclohexane) to give the title compound (6.1 mg, 76%) as a white solid. LCMS (Method A): R$_T$=1.42 min, m/z=352, 354 [M+H]⁺.

Step 3: tert-Butyl 4-(4-((6-(2,6-dichlorophenyl)-8-methyl-5-oxo-5,6-dihydropyrido[4,3-d]pyrimidin-2-yl)amino)phenyl)piperazine-1-carboxylate: mCPBA (<77% pure) (4.5 mg, assumed 0.020 mmol) in DCM (0.5 ml) was added to a stirred solution of 6-(2,6-dichlorophenyl)-8-methyl-2-(methylthio)pyrido[4,3-d]pyrimidin-5(6H)-one (6.1 mg, 0.017 mmol) in toluene (1.0 mL) at RT under nitrogen. After 1.5 h, DIPEA (9.0 μL, 0.052 mmol) and tert-butyl 4-(4-aminophenyl)piperazine-1-carboxylate (5.3 mg, 0.019 mmol) [commercially available] in toluene (0.5 ml) were added, successively, and the temperature was increased to 60° C. After 16 h, the reaction mixture was allowed to cool to RT, and was loaded directly onto a column and purified by flash chromatography (0-100%, EtOAc in cyclohexane) to give the title compound (5.4 mg, 54%) as a yellow oil. LCMS (Method A): R$_T$=1.61 min, m/z=581, 583 [M+H]⁺.

Step 4: 6-(2,6-Dichlorophenyl)-8-methyl-2-((4-(piperazin-1-yl)phenyl)amino)pyrido[4,3-d]pyrimidin-5(6H)-one: TFA (1.0 mL, 13.0 mmol) was added to a stirred solution of tert-butyl 4-(4-((6-(2,6-dichlorophenyl)-8-methyl-5-oxo-5,6-dihydropyrido[4,3-d]pyrimidin-2-yl)amino)phenyl)piperazine-1-carboxylate (5.4 mg, 9.29 μmol) in DCM (1.0 mL) at RT under nitrogen. After 15 min, the solvents were removed in vacuo and the remaining residue was partitioned between DCM and saturated sodium bicarbonate (aq) solution, separated, extracted (DCM×2), dried (Phase Separator), and the solvents were removed in vacuo. The remaining residue was purified by flash chromatography using a KP-NH column (0-100% EtOAc in cyclohexane; then 10% MeOH in EtOAc) to give material that required purification by preparative HPLC. The pure fractions were concentrated to give the title compound (2.0 mg, 44%) as a yellow solid. LCMS (Method A): R$_T$=0.85 min, m/z=481, 483 [M+H]⁺. ¹H NMR (500 MHz, methanol-d4): δ 9.19 (s, 1H), 7.77 (br s, 2H), 7.65-7.60 (m, 2H), 7.52 (dd, 1H), 7.35 (s, 1H), 7.02 (d, 2H), 3.14 (t, 4H), 3.01 (t, 4H), 2.30 (s, 3H).

Example 3

6-(2-Chloropyridin-3-yl)-2-((4-(piperazin-1-yl)phenyl)amino)pyrido[4,3-d]pyrimidin-5(6H)-one

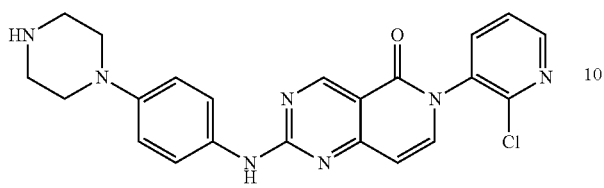

Step 1: N-(2-Chloropyridin-3-yl)-4-methyl-2-(methylthio)pyrimidine-5-carboxamide: Phosphorus trichloride (0.047 mL, 0.543 mmol) was added to a stirred solution of 4-methyl-2-(methylthio)pyrimidine-5-carboxylic acid (100 mg, 0.543 mmol) and 2-chloropyridin-3-amine (69.8 mg, 0.543 mmol) in chlorobenzene (2.0 mL) at 135° C. under nitrogen. After 16 h, the solvents were removed in vacuo and the remaining residue was purified by flash chromatography (0-100%, EtOAc in cyclohexane) to give the title compound (53.3 mg, 33%) as a pale yellow solid. LCMS (Method A): $R_T$=0.98 min, m/z=295 [M+H]$^+$.

Step 2: 6-(2-Chloropyridin-3-yl)-2-(methylthio)pyrido[4,3-d]pyrimidin-5(6H)-one: DMF-DMA (0.048 mL, 0.362 mmol) was added to a stirred solution of N-(2-chloropyridin-3-yl)-4-methyl-2-(methylthio)pyrimidine-5-carboxamide (53.3 mg, 0.181 mmol) in DMF (2.0 mL) at RT under nitrogen. The reaction mixture was heated to 150° C. After 20 h, the reaction mixture was partitioned using diethyl ether and 1:1 brine/water, separated, extracted (2×diethyl ether), the combined organic phase was dried (Phase Separator), the solvents were removed in vacuo, and the remaining residue was purified by flash chromatography (0-100%, EtOAc in cyclohexane) to give the title compound (18.2 mg, 33%) as a pale yellow solid. LCMS (Method A): $R_T$=1.00 min, m/z=305 [M+H]$^+$.

Step 3: tert-Butyl 4-(4-((6-(2-chloropyridin-3-yl)-5-oxo-5,6-dihydropyrido[4,3-d]pyrimidin-2-yl)amino)phenyl)piperazine-1-carboxylate: mCPBA (<77% pure) (15.5 mg, assumed 0.069 mmol) in DCM (0.5 mL) was added to a stirred solution of 6-(2-chloropyridin-3-yl)-2-(methylthio)pyrido[4,3-d]pyrimidin-5(6H)-one (18.2 mg, 0.060 mmol) in toluene (1.5 mL) at RT under nitrogen. After 15 min, DIPEA (0.031 mL, 0.179 mmol) and tert-butyl 4-(4-aminophenyl)piperazine-1-carboxylate (18.2 mg, 0.066 mmol) [commercially available] were added, successively, and the temperature was increased to 60° C. After 16 h, the reaction mixture was allowed to cool to RT, and was loaded onto a KP-NH column and purified by flash chromatography (0-100%, EtOAc in cyclohexane) to give the title compound (14.3 mg, 45%) as a yellow solid. LCMS (Method A): $R_T$=1.33 min, m/z=534 [M+H]$^+$.

Step 4: 6-(2-Chloropyridin-3-yl)-2-((4-(piperazin-1-yl)phenyl)amino)pyrido[4,3-d]pyrimidin-5(6H)-one: TFA (2.0 mL, 26.0 mmol) was added to a stirred solution of tert-butyl 4-(4-((6-(2-chloropyridin-3-yl)-5-oxo-5,6-dihydropyrido[4,3-d]pyrimidin-2-yl)amino)phenyl)piperazine-1-carboxylate (14.3 mg, 0.027 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue purified by preparative HPLC to give the title compound (7.0 mg, 60%) as a pale yellow solid. LCMS (Method A): $R_T$=0.62 min, m/z=434 [M+H]$^+$. $^1$H NMR (500 MHz, methanol-d4): δ 9.18 (s, 1H), 8.53 (dd, 1H), 8.01 (dd, 1H), 7.65 (br d, 2H), 7.60 (dd, 1H), 7.57 (d, 1H), 7.04-6.98 (m, 2H), 6.58 (d, 1H), 3.14 (t, 4H), 3.00 (t, 4H).

Example 4

6-(2,6-Dichlorophenyl)-2-((4-(2-(diethylamino)ethoxy)phenyl)amino)pyrido[4,3-d]pyrimidin-5(6H)-one

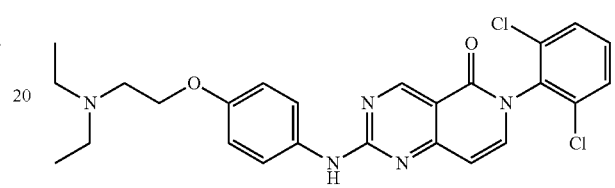

mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50.0 mg, 0.148 mmol) in toluene (1.5 mL) at RT under nitrogen. After 15 min, DIPEA (0.077 mL, 0.444 mmol) and 4-(2-(diethylamino)ethoxy)aniline (33.9 mg, 0.163 mmol) [commercially available] were added, successively, and the temperature was increased to 60° C. After 16 h, the reaction mixture was allowed to cool to RT, and was loaded onto a KP-NH column and purified by flash chromatography (0-100%, EtOAc in cyclohexane; then 10% MeOH in EtOAc) to give the title compound (40.6 mg, 52%) as a pale yellow solid. LCMS (Method A): $R_T$=0.87 min, m/z=498, 500 [M+H]$^+$. $^1$H NMR (500 MHz, methanol-d4): δ 9.20 (s, 1H), 7.72-7.61 (m, 4H), 7.53 (dd, 1H), 7.48 (d, 1H), 6.99-6.95 (m, 2H), 6.60 (d, 1H), 4.15 (t, 2H), 3.00 (br s, 2H), 2.77 (br d, 4H), 1.14 (t, 6H).

Example 5

2-((4-(4-Acetylpiperazin-1-yl)phenyl)amino)-6-(2,6-dichlorophenyl)pyrido[4,3-d]pyrimidin-5(6H)-one

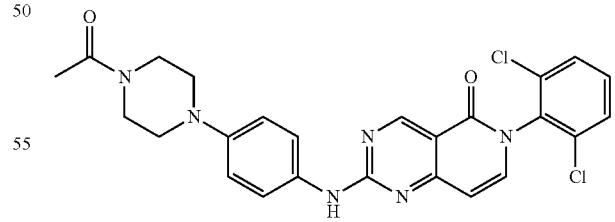

mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50.0 mg, 0.148 mmol) in toluene (1.5 mL) at RT under nitrogen. After 15 min, DIPEA (0.077 mL, 0.444 mmol) and 1-(4-(4-aminophenyl)piperazin-1-yl)ethanone (35.7 mg, 0.163 mmol) [commercially available] were added, successively, and the temperature was increased to 60° C. After 22 h, the reaction mixture was allowed to cool to RT, and was loaded onto a KP-NH column and purified by flash chromatography (0-100%, EtOAc in cyclohexane) to give material that was purified further by trituration with methanol to furnish the title compound (47.5 mg, 63%) as a bright yellow solid. LCMS (Method A): R$_T$=1.11 min, m/z=509, 511 [M+H]$^+$. $^1$H NMR (500 MHz, CDCl$_3$): δ 9.32 (s, 1H), 7.61 (br d, 2H), 7.55-7.44 (m, 3H), 7.38 (t, 1H), 7.15 (d, 1H), 6.97 (d, 2H), 6.52 (d, 1H), 3.79 (s, 2H), 3.64 (s, 2H), 3.16 (br d, 4H), 2.15 (s, 3H).

Example 6

6-(2,6-Dichlorophenyl)-2-((4-(1,1-dioxidothiomorpholino)phenyl)amino)pyrido[4,3-d]pyrimidin-5(6H)-one

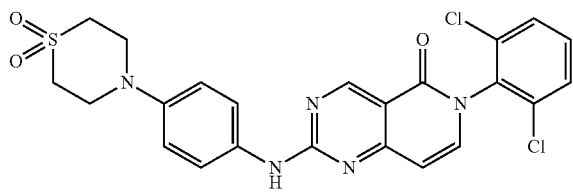 [SMILES: O=c1c2cnc(Nc3ccc(N4CCS(=O)(=O)CC4)cc3)nc2ccn1-c1c(Cl)cccc1Cl]

mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50.0 mg, 0.148 mmol) in toluene (1.5 mL) at RT under nitrogen. After 15 min, DIPEA (0.077 mL, 0.444 mmol) and 4-(4-aminophenyl)thiomorpholine 1,1-dioxide (36.8 mg, 0.163 mmol) [commercially available] were added, successively, and the temperature was increased to 60° C. After 22 h, the reaction mixture was allowed to cool to RT, and was loaded onto a KP-NH column and purified by flash chromatography (0-100%, EtOAc in cyclohexane) to give the title compound (41.2 mg, 54%) as a bright yellow solid. LCMS (Method A): R$_T$=1.15 min, m/z=516, 518 [M+H]$^+$. $^1$H NMR (500 MHz, methanol-d4): δ 9.19 (s, 1H), 7.69 (br d, 2H), 7.65-7.62 (m, 2H), 7.52 (dd, 1H), 7.48 (d, 1H), 7.10-7.06 (m, 2H), 6.59 (d, 1H), 3.83 (t, 4H), 3.17 (t, 4H).

Example 7

6-(2,6-Dichlorophenyl)-2-((3-methyl-4-(piperazin-1-yl)phenyl)amino)pyrido[4,3-d]pyrimidin-5(6H)-one

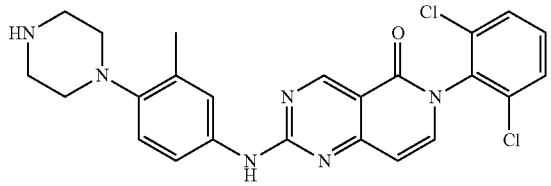

Step 1: tert-Butyl 4-(4-((6-(2,6-dichlorophenyl)-5-oxo-5,6-dihydropyrido[4,3-d]pyrimidin-2-yl)amino)-2-methylphenyl)piperazine-1-carboxylate: mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50 mg, 0.148 mmol) in toluene (2.0 mL) at RT under nitrogen. After 15 min, DIPEA (0.077 mL, 0.444 mmol) and tert-butyl 4-(4-amino-2-methylphenyl)piperazine-1-carboxylate (47.4 mg, 0.163 mmol) [commercially available] were added, successively, and the temperature was increased to 60° C. After 18 h, the reaction mixture was allowed to cool to RT, and was loaded onto a KP-NH column and purified by flash chromatography (0-50%, EtOAc in cyclohexane) to give the title compound (59.7 mg, 69%) as a pale yellow solid. LCMS (Method A): R$_T$=1.68 min, m/z=581, 583 [M+H]$^+$.

Step 2: 6-(2,6-Dichlorophenyl)-2-((3-methyl-4-(piperazin-1-yl)phenyl)amino)pyrido[4,3-d]pyrimidin-5(6H)-one: TFA (2.0 mL, 26.0 mmol) was added to a stirred solution of tert-butyl 4-(4-((6-(2,6-dichlorophenyl)-5-oxo-5,6-dihydropyrido[4,3-d]pyrimidin-2-yl)amino)-2-methylphenyl)piperazine-1-carboxylate (59.7 mg, 0.103 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), and the solvents were removed in vacuo to give the title compound (46.4 mg, 93%) as a yellow solid. LCMS (Method A): R$_T$=0.90 min, m/z=481, 483 [M+H]$^+$. $^1$H NMR (500 MHz, methanol-d4): δ 9.20 (s, 1H), 7.66-7.58 (m, 3H), 7.55-7.50 (m, 2H), 7.48 (d, 1H), 7.08 (d, 1H), 6.61 (d, 1H), 3.03 (t, 4H), 2.91 (t, 4H), 2.35 (s, 3H).

Example 8

6-(2,6-Dichlorophenyl)-2-((3-(hydroxymethyl)-4-(4-methylpiperazin-1-yl)phenyl)amino)pyrido[4,3-d]pyrimidin-5(6H)-one

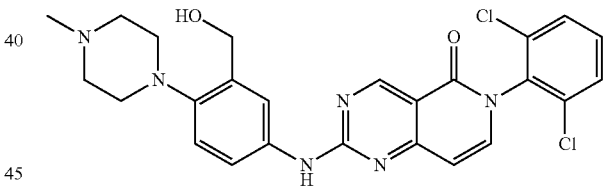

mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50 mg, 0.148 mmol) in toluene (2.0 mL) at RT under nitrogen. After 15 min, DIPEA (0.077 mL, 0.444 mmol) and (5-amino-2-(4-methylpiperazin-1-yl)phenyl)methanol (36.0 mg, 0.163 mmol) [commercially available] were added, successively, and the temperature was increased to 60° C. After 16 h, the reaction mixture was allowed to cool to RT, and was loaded onto a KP-NH column and purified by flash chromatography (0-100%, EtOAc in cyclohexane; then 10% MeOH in EtOAc) to give material that required further purification by preparative HPLC to give the title compound (25.9 mg, 34%) as a pale yellow solid. LCMS (Method A): R$_T$=0.80 min, m/z=511, 513 [M+H]$^+$. $^1$H NMR (500 MHz, CDCl$_3$): δ 9.34 (s, 1H), 7.67 (dd, 1H), 7.53-7.48 (m, 3H), 7.42 (br s, 1H), 7.38 (dd, 1H), 7.16 (d, 1H), 6.54 (d, 1H), 5.40 (br s, 1H), 4.83 (s, 2H), 3.03 (t, 4H), 2.63 (br s, 4H), 2.37 (s, 3H).

Example 9

8-Bromo-6-(2,6-dichlorophenyl)-2-((4-(piperazin-1-yl)phenyl)amino)pyrido[4,3-d]pyrimidin-5(6H)-one

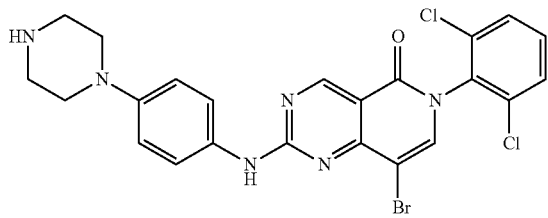 [SMILES: O=c1c2cnc(Nc3ccc(N4CCNCC4)cc3)nc2c(Br)cn1-c1c(Cl)cccc1Cl]

Step 1: tert-Butyl 4-(4-((8-bromo-6-(2,6-dichlorophenyl)-5-oxo-5,6-dihydropyrido[4,3-d]pyrimidin-2-yl)amino)phenyl)piperazine-1-carboxylate: mCPBA (<77% pure) (61.1 mg, assumed 0.273 mmol) in DCM (0.5 mL) was added to a stirred solution of 8-bromo-6-(2,6-dichlorophenyl)-2-(methylthio)pyrido[4,3-d]pyrimidin-5(6H)-one (98.4 mg, 0.236 mmol) in toluene (4.0 mL) at RT under nitrogen. After 20 min, DIPEA (0.124 mL, 0.708 mmol) and tert-butyl 4-(4-aminophenyl)piperazine-1-carboxylate (72.0 mg, 0.260 mmol) [commercially available] were added, successively, and the temperature was increased to 60° C. After 16 h, the reaction mixture was allowed to cool to RT, and was loaded onto a KP-NH column and purified by flash chromatography (0-50%, EtOAc in cyclohexane) to give the title compound (125 mg, 82%) as a brown solid. LCMS (Method A): $R_T$=1.67 min, m/z=647 [M+H]$^+$.

Step 2: 8-Bromo-6-(2,6-dichlorophenyl)-2-((4-(piperazin-1-yl)phenyl)amino)pyrido[4,3-d]pyrimidin-5(6H)-one: TFA (0.5 mL, 6.49 mmol) was added to a stirred solution of tert-butyl 4-(4-((8-bromo-6-(2,6-dichlorophenyl)-5-oxo-5,6-dihydropyrido[4,3-d]pyrimidin-2-yl)amino)phenyl)piperazine-1-carboxylate (10.0 mg, 0.015 mmol) in DCM (0.5 mL) at RT under nitrogen. After 30 min, the solvents were removed in vacuo and the remaining residue was partitioned between DCM and satd sodium bicarbonate (aq) solution, separated, extracted (2×DCM), dried (Phase Separator), the solvents were removed in vacuo, and the remaining residue was loaded onto a KP-NH column and purified by flash chromatography (0-100%, EtOAc in cyclohexane; then 0-5% MeOH in EtOAc) to give the title compound (2.5 mg, 29%) as a yellow solid. LCMS (Method A): $R_T$=0.97 min, m/z=547 [M+H]$^+$. $^1$H NMR (500 MHz, methanol-d4): δ 9.16 (s, 1H), 8.05-7.88 (m, 3H), 7.64 (d, 2H), 7.54 (dd, 1H), 7.02 (d, 2H) 3.14 (t, 4H), 3.00 (t, 4H).

Example 10

6-(2,6-Dichlorophenyl)-2-((4-(1-methylpiperidin-4-yl)phenyl)amino)pyrido[4,3-d]pyrimidin-5(6H)-one, HCl

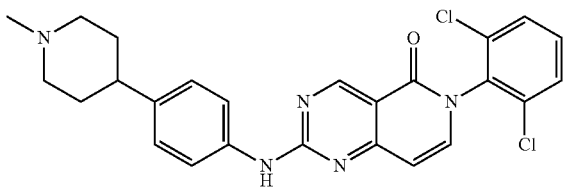

mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50 mg, 0.148 mmol) in toluene (2.0 mL) at RT under nitrogen. After 15 min, DIPEA (0.077 mL, 0.444 mmol) and 4-(1-methylpiperidin-4-yl)aniline (30.9 mg, 0.163 mmol) [commercially available] were added, successively, and the temperature was increased to 60° C. After 16 h, the reaction mixture was allowed to cool to RT, and was loaded onto a KP-NH column and purified by flash chromatography (0-100%, EtOAc in cyclohexane) to give material that required further purification by preparative HPLC. The pure fractions were concentrated in vacuo and the remaining residue was dissolved in methanol (25 mL) and a solution of acetyl chloride (0.032 mL, 0.444 mmol) in methanol (1.5 mL) [ca. 3 eq. of a 1M HCl in methanol solution] was added dropwise with stirring. After 30 min, the solvents were removed in vacuo and the remaining residue was freeze-dried to give the title compound (36.2 mg, 51%) as a yellow solid. LCMS (Method A): $R_T$=0.89 min, m/z=480, 482 [M+H]$^+$. $^1$H NMR (500 MHz, methanol-d4): δ 9.24 (s, 1H), 7.79 (d, 2H), 7.64 (d, 2H), 7.55-7.50 (m, 2H), 7.29 (d, 2H), 6.63 (d, 1H) 3.63 (br d, 2H), 3.18 (br t, 2H), 2.95-2.87 (m, 4H), 2.16 (br d, 2H), 2.02-1.92 (m, 2H).

Example 11

6-(2,6-Dichlorophenyl)-2-((4-(2-(dimethylamino)ethyl)phenyl)amino)pyrido[4,3-d]pyrimidin-5(6H)-one, HCl

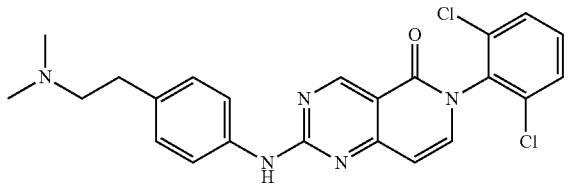 [SMILES: CN(C)CCc1ccc(Nc2ncc3c(=O)n(-c4c(Cl)cccc4Cl)ccc3n2)cc1]

mCPBA (<77% pure) (38.3 mg, assumed 0.171 mmol) in DCM (0.5 mL) was added to a stirred solution of 6-(2,6-dichlorophenyl)-2-(methylthio)pyrido[4,3-d]pyrimidin-5(6H)-one (50 mg, 0.148 mmol) in toluene (2.0 mL) at RT under nitrogen. After 30 min, DIPEA (0.077 mL, 0.444 mmol) and 4-(2-(dimethylamino)ethyl)aniline (26.7 mg, 0.163 mmol) [commercially available] were added, successively, and the temperature was increased to 60° C. After 16 h, the reaction mixture was allowed to cool to RT, and was loaded onto a KP-NH column and purified by flash chromatography (0-50%, EtOAc in cyclohexane). The resultant material required further purification by preparative HPLC. The pure fractions were concentrated in vacuo and the residue was dissolved in methanol (25 ml) and a solution of acetyl chloride (0.032 mL, 0.444 mmol) in methanol (1.5 ml) [ca. 3 eq. of a 1M HCl in methanol solution] was added dropwise with stirring. After 30 min, the solvents were removed in vacuo and the remaining residue was freeze-dried to give the title compound (31.2 mg, 46%) as a yellow solid. LCMS (Method A): $R_T$=0.79 min, m/z=454, 456 [M+H]$^+$. $^1$H NMR (500 MHz, methanol-d4): δ 9.25 (s, 1H), 7.82 (d, 2H), 7.64 (d, 2H), 7.56-7.51 (m, 2H), 7.33 (d, 2H), 6.63 (d, 1H) 3.44-3.39 (m, 2H), 3.09-3.04 (m, 2H), 2.96 (s, 6H).

Example 12

6-(2,6-Dichlorophenyl)-2-((3-methoxy-4-(4-methyl-piperazin-1-yl)phenyl)amino)pyrido[4,3-d]pyrimidin-5(6H)-one, HCl

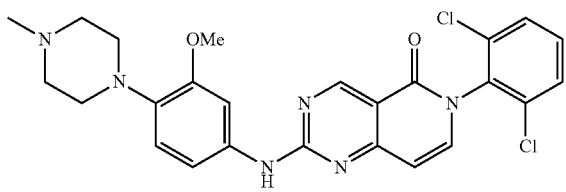 [SMILES: COc1cc(Nc2ncc3c(=O)n(-c4c(Cl)cccc4Cl)ccc3n2)ccc1N1CCN(C)CC1]

mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (2.0 mL) at RT under nitrogen. After 15 min, DIPEA (0.155 mL, 0.887 mmol) and 3-methoxy-4-(4-methylpiperazin-1-yl)aniline (72.0 mg, 0.325 mmol) [commercially available] were added, successively, and the temperature was increased to 60° C. After 16 h, the reaction mixture was allowed to cool to RT, and was loaded onto a KP-NH column and purified by flash chromatography (0-100%, EtOAc in cyclohexane). The pure fractions were concentrated in vacuo and the remaining residue was dissolved in methanol (35 ml) and acetyl chloride (0.105 mL, 1.478 mmol) in methanol (1.5 ml) was added [ca. 5 eq. of a 1M HCl in MeOH solution] with stirring. After 30 min, the solvents were removed in vacuo and the remaining residue was freeze-dried to give material that required further purification. The residue was dissolved in methanol and diethyl ether was added to precipitate the product from solution. The precipitate was triturated using further diethyl ether and the resultant material was freeze-dried to give the title compound (41.4 mg, 27%) as a pale yellow solid. LCMS (Method A): $R_T$=0.81 min, m/z=511, 513 [M+H]$^+$. $^1$H NMR (500 MHz, methanol-d4): δ 9.23 (s, 1H), 7.70-7.62 (m, 3H), 7.55-7.50 (m, 2H), 3.93 (s, 3H), 3.58 (br d, 4H), 3.33 (apparent t, 2H) overlapping solvent, 3.05 (t, 2H), 2.98 (s, 3H).

Example 13

6-(2,6-Dichlorophenyl)-2-((3-methoxy-4-(piperazin-1-yl)phenyl)amino)pyrido[4,3-d]pyrimidin-5(6H)-one, HCl

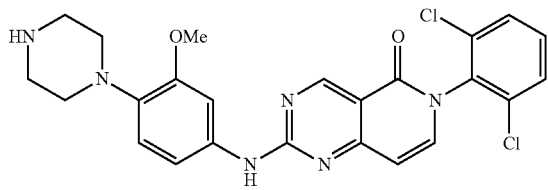 [SMILES: COc1cc(Nc2ncc3c(=O)n(-c4c(Cl)cccc4Cl)ccc3n2)ccc1N1CCNCC1]

Step 1: tert-Butyl 4-(4-((6-(2,6-dichlorophenyl)-5-oxo-5,6-dihydropyrido[4,3-d]pyrimidin-2-yl)amino)-2-methoxyphenyl)piperazine-1-carboxylate: mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, DIPEA (0.155 mL, 0.887 mmol) and tert-butyl 4-(4-amino-2-methoxyphenyl)piperazine-1-carboxylate (100 mg, 0.325 mmol) [commercially available] were added, successively, and the temperature was increased to 60° C. After 16 h, the reaction mixture was allowed to cool to RT, and was loaded onto a KP-NH column and purified by flash chromatography (0-100%, EtOAc in cyclohexane) to give the title compound (149 mg, 84%) as a yellow solid. LCMS (Method A): $R_T$=1.51 min, m/z=597, 599 [M+H]$^+$.

Step 2: 6-(2,6-Dichlorophenyl)-2-((3-methoxy-4-(piperazin-1-yl)phenyl)amino)pyrido[4,3-d]pyrimidin-5(6H)-one, HCl: TFA (2.0 mL, 26.0 mmol) was added to a stirred solution of tert-butyl 4-(4-((6-(2,6-dichlorophenyl)-5-oxo-5,6-dihydropyrido[4,3-d]pyrimidin-2-yl)amino)-2-methoxyphenyl)piperazine-1-carboxylate (149 mg, 0.249 mmol) in DCM (2.0 mL) at RT under nitrogen. After 1 h, the solvents were removed in vacuo and the remaining residue was partitioned between DCM and satd sodium bicarbonate (aq) solution, separated, extracted (DCM×2), dried (Phase Separator), and the solvents were removed in vacuo. The remaining residue was dissolved in methanol and 5 eq of a 1M HCl in methanol solution [Note: prepared by adding AcCl to MeOH] was added. After stirring for 30 min, the solvents were removed in vacuo and the remaining residue was freeze-dried to give material that required further purification. The material was dissolved in MeOH and diethyl ether added to crash out the product. The resulting precipitate was triturated using further diethyl ether and the residual solvents were removed in vacuo. The remaining residue was freeze-dried to give the title compound (101 mg, 76%) as a pale yellow solid. LCMS (Method A): $R_T$=0.81 min, m/z=497, 499 [M+H]$^+$. $^1$H NMR (500 MHz, methanol-d4): δ 9.25 (s, 1H), 7.70-7.62 (m, 3H), 7.57-7.52 (m, 2H), 7.35 (dd, 1H), 7.07 (d, 1H), 6.64 (d, 1H), 3.95 (s, 3H), 3.41 (t, 4H), 3.34 (t, 4H).

Example 14

6-(2,6-Dichlorophenyl)-8-(3-hydroxyprop-1-yn-1-yl)-2-((3-methyl-4-(piperazin-1-yl)phenyl)amino)pyrido[4,3-d]pyrimidin-5(6H)-one

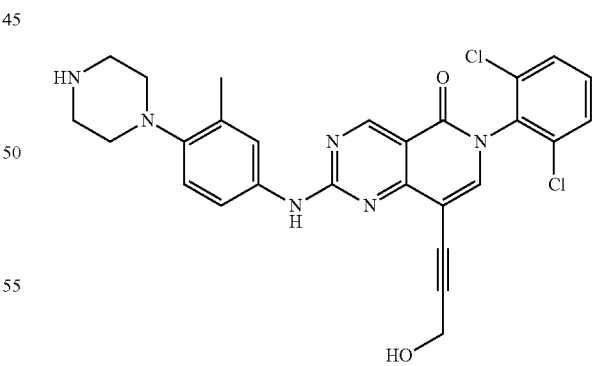

Step 1: 6-(2,6-Dichlorophenyl)-2-(methylthio)-8-(3-((tetrahydro-2H-pyran-2-yl)oxy)prop-1-yn-1-yl)pyrido[4,3-d]pyrimidin-5(6H)-one: Copper(I) iodide (0.6 mg, 3.0 µmol) and bis(triphenylphosphine)palladium(II) chloride (4.2 mg, 6.0 µmol) were added to a pre-degassed solution of 8-bromo-6-(2,6-dichlorophenyl)-2-(methylthio)pyrido[4,3-d]pyrimidin-5(6H)-one (50 mg, 0.120 mmol), 2-(prop-2-yn-1-yloxy)tetrahydro-2H-pyran (33.6 mg, 0.240 mmol) and tetrabutylammonium iodide (89 mg, 0.240 mmol) in triethylamine (0.2 mL, 1.44 mmol)/DMF (1.0 mL) in a 10 mL vial. The reaction vessel was sealed and heated under microwave conditions (CEM Explorer/Discover) at 100° C. (80 W ceiling) for 15 min. Due to incomplete reaction, the reaction was rerun at 100° C. (80 W ceiling) for 15 min. Due to incomplete reaction, the reaction was rerun at 120° C. for 20 min. The reaction mixture was partitioned between diethyl ether and 1:1, water/brine, separated, extracted (diethyl ether×3), the organic phase was dried (Phase Separator), the solvents were removed in vacuo, and the remaining residue was purified by flash chromatography (0-100%, EtOAc in cyclohexane) to give the title compound (34.3 mg, 60%) as a yellow oil. LCMS (Method A): $R_T$=1.61 min, m/z=476, 478 [M+H]$^+$.

Step 2: tert-Butyl 4-(4-((6-(2,6-dichlorophenyl)-5-oxo-8-(3-((tetrahydro-2H-pyran-2-yl)oxy)prop-1-yn-1-yl)-5,6-dihydropyrido[4,3-d]pyrimidin-2-yl)amino)-2-methylphenyl)piperazine-1-carboxylate: mCPBA (<77% pure) (18.6 mg, assumed 0.083 mmol) in DCM (0.5 mL) was added to a stirred solution of 6-(2,6-dichlorophenyl)-2-(methylthio)-8-(3-((tetrahydro-2H-pyran-2-yl)oxy)prop-1-yn-1-yl)pyrido[4,3-d]pyrimidin-5(6H)-one (34.3 mg, 0.072 mmol) in toluene (3.0 mL) at RT under nitrogen. After 20 min, DIPEA (0.038 mL, 0.216 mmol) and tert-butyl 4-(4-amino-2-methylphenyl)piperazine-1-carboxylate (21.0 mg, 0.072 mmol) [commercially available] were added, successively, and the temperature was increased to 60° C. After 16 h, the reaction mixture was cooled and loaded directly onto a KP-NH column and purified by flash chromatography (0-30%, EtOAc in cyclohexane) to give the title compound (15.5 mg, 30%) as a pale yellow solid. LCMS (Method A): $R_T$=1.87 min, m/z=719, 721 [M+H]$^+$.

Step 3: 6-(2,6-Dichlorophenyl)-8-(3-hydroxyprop-1-yn-1-yl)-2-((3-methyl-4-(piperazin-1-yl)phenyl)amino)pyrido[4,3-d]pyrimidin-5(6H)-one: TFA (1.0 mL, 13.0 mmol) was added to a stirred solution of tert-butyl 4-(4-((6-(2,6-dichlorophenyl)-5-oxo-8-(3-((tetrahydro-2H-pyran-2-yl)oxy)prop-1-yn-1-yl)-5,6-dihydropyrido[4,3-d]pyrimidin-2-yl)amino)-2-methylphenyl)piperazine-1-carboxylate (15.5 mg, 0.022 mmol) in DCM (1.0 mL) at RT under nitrogen. After 4 h, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography using a KP-NH column (0-100% EtOAc in cyclohexane; then 10% MeOH in EtOAc) to give the title compound (6.5 mg, 56%) as a yellow solid. LCMS (Method A): $R_T$=0.82 min, m/z=535, 537 [M+H]$^+$. $^1$H NMR (500 MHz, methanol-d4): δ 9.19 (s, 1H), 8.00-7.74 (m, 3H), 7.64 (d, 2H), 7.54 (t, 1H), 7.09 (d, 1H), 4.50 (s, 2H), 3.04 (t, 4H), 2.92 (t, 4H), 2.37 (s, 3H).

Example 15

6-(2,6-Dichlorophenyl)-2-((4-(4-methylpiperazin-1-yl)phenyl)amino)pyrido[4,3-d]pyrimidin-5(6H)-one

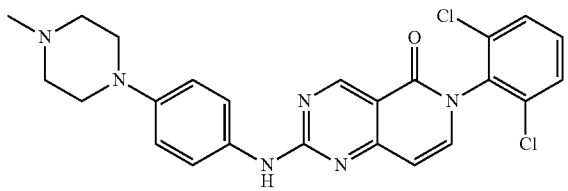 [SMILES: CN1CCN(c2ccc(Nc3ncc4c(=O)n(-c5c(Cl)cccc5Cl)ccc4n3)cc2)CC1]

mCPBA (<77% pure) (57.4 mg, assumed 0.256 mmol) in DCM (0.5 mL) was added to a stirred solution of 6-(2,6-dichlorophenyl)-2-(methylthio)pyrido[4,3-d]pyrimidin-5(6H)-one (75 mg, 0.222 mmol) in toluene (3.0 mL) at RT under nitrogen. After 30 min, further mCPBA (20 mg) was added. After a further 15 min, DIPEA (0.116 mL, 0.665 mmol) and 4-(4-methylpiperazin-1-yl)aniline (42.4 mg, 0.222 mmol) [commercially available] were added, successively, and the temperature was increased to 60° C. After 16 h, the reaction mixture was cooled and loaded directly onto a KP-NH column and purified by flash chromatography (0-100%, EtOAc in cyclohexane) to give the title compound (50.8 mg, 47%) as a yellow solid. LCMS (Method A): $R_T$=0.78 min, m/z=481, 483 [M+H]$^+$. $^1$H NMR (500 MHz, methanol-d4): δ 9.19 (s, 1H), 7.68-7.61 (m, 4H), 7.52 (dd, 1H), 7.47 (d, 1H), 7.03-6.99 (m, 2H), 6.60 (d, 1H), 3.21 (t, 4H), 2.64 (t, 4H), 2.36 (s, 3H).

Example 16

6-(2,6-Dichlorophenyl)-2-((4-(2-(methylamino)ethoxy)phenyl)amino)pyrido[4,3-d]pyrimidin-5(6H)-one, HCl

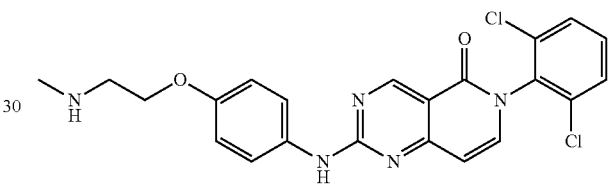

Step 1: tert-Butyl (2-(4-((6-(2,6-dichlorophenyl)-5-oxo-5,6-dihydropyrido[4,3-d]pyrimidin-2-yl)amino)phenoxy)ethyl)(methyl)carbamate: mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, further mCPBA (30 mg) was added. After a further 15 min, DIPEA (0.155 mL, 0.887 mmol) and tert-butyl (2-(4-aminophenoxy)ethyl)(methyl)carbamate (79 mg, 0.296 mmol) [prepared according to the literature procedure in WO 2011/140009 (intermediate in Example 64)] in toluene (0.5 mL) were added, successively, and the temperature was increased to 60° C. After 16 h, the reaction mixture was cooled and loaded directly onto a KP-NH column and purified by flash chromatography (0-50%, EtOAc in cyclohexane) to give the title compound (58.3 mg, 0.105 mmol, 35%) as a pale yellow solid. LCMS (Method A): $R_T$=1.54 min, m/z=556, 558 [M+H]$^+$.

Step 2: 6-(2,6-Dichlorophenyl)-2-((4-(2-(methylamino)ethoxy)phenyl)amino)pyrido[4,3-d]pyrimidin-5(6H)-one, HCl: TFA (2.0 mL, 26.0 mmol) was added to a stirred solution of tert-butyl (2-(4-((6-(2,6-dichlorophenyl)-5-oxo-5,6-dihydropyrido[4,3-d]pyrimidin-2-yl)amino)phenoxy)ethyl)(methyl)carbamate (58.3 mg, 0.105 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was dissolved in MeOH (10 mL) and was treated with a 5 equiv. of a ca. 1M HCl in MeOH solution (previously prepared by addition of acetyl chloride (0.037 mL, 0.524 mmol) to 0.5 mL MeOH). After 30 min, the solvents were removed in vacuo and the remaining residue was freeze-dried to give the title compound (48.7 mg, 90%) as a dark yellow solid. LCMS (Method X): $R_T$=0.78 min, m/z=456, 458 [M+H]$^+$. $^1$H NMR (500 MHz, methanol-d4): δ 9.22 (s, 1H), 7.72 (br d, 2H), 7.64 (d, 2H), 7.56-7.50 (m, 2H), 7.08-7.03 (m, 2H), 6.60 (d, 1H), 4.30 (t, 2H), 3.47 (t, 2H), 2.81 (s, 3H).

Example 17

6-(2,6-Dichlorophenyl)-2-((4-(4-isopropylpiperazin-1-yl)phenyl)amino)pyrido[4,3-d]pyrimidin-5(6H)-one

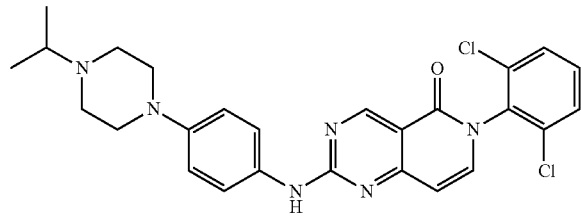 [SMILES: CC(C)N1CCN(c2ccc(Nc3ncc4c(=O)n(-c5c(Cl)cccc5Cl)ccc4n3)cc2)CC1]

mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (2.0 mL) at RT under nitrogen. After 30 min, DIPEA (0.155 mL, 0.887 mmol) and 4-(4-isopropylpiperazin-1-yl)aniline (71.3 mg, 0.325 mmol) [prepared according the literature procedure in WO 2008/065199 (Examples D.5 and D.6)] were added, successively, and the temperature was increased to 60° C. After 16 h, the reaction mixture was allowed to cool to RT, and was loaded onto a KP-NH column and purified by flash chromatography (0-100%, EtOAc in cyclohexane). The resultant material required further purification by preparative HPLC. The resultant material required further purification by flash chromatography (0-30%, EtOAc in cyclohexane) to give the title compound (59.0 mg, 39%) as a yellow solid. LCMS (Method A): $R_T$=0.84 min, m/z=509, 511 [M+H]$^+$. $^1$H NMR (500 MHz, methanol-d4): δ 9.19 (s, 1H), 7.68-59 (m, 4H), 7.52 (dd, 1H), 7.47 (d, 1H), 7.04-6.99 (m, 2H), 6.60 (d, 1H), 3.21 (t, 4H), 2.79-2.69 (m, 5H), 1.15 (s, 3H), 1.13 (s, 3H).

Example 18

6-(2,6-Dichlorophenyl)-2-((3-(hydroxymethyl)-4-(piperazin-1-yl)phenyl)amino)pyrido[4,3-d]pyrimidin-5(6H)-one

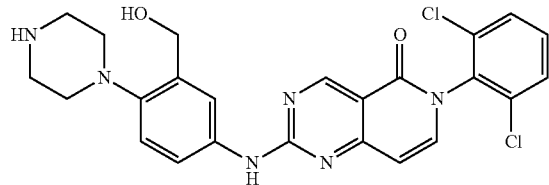 [SMILES: O=c1c2cnc(Nc3ccc(N4CCNCC4)c(CO)c3)nc2ccn1-c1c(Cl)cccc1Cl]

Step 1: tert-Butyl 4-(4-amino-2-(hydroxymethyl)phenyl)piperazine-1-carboxylate: Ammonium formate (1.47 g, 23.2 mmol) was added carefully [Note: exothermic] to a stirred solution of tert-butyl 4-(2-(hydroxymethyl)-4-nitrophenyl)piperazine-1-carboxylate (1.57 g, 4.65 mmol) [prepared according to the literature procedure in J. Med. Chem., 2011, 54(13), 4638-4658 (Compounds 9b and 10d)] and 10% palladium on carbon (0.247 g, 0.232 mmol) in ethanol (15 mL) in a 100 mL round-bottomed flask at RT under nitrogen. After 16 h, the reaction mixture was filtered through Celite® and the solvents were removed in vacuo. The remaining residue was partitioned between satd sodium bicarbonate (aq) solution (30 mL) and DCM (30 mL), separated, and extracted using further DCM (2×15 mL). The combined organic phase was dried (Phase Separator) and the solvents were removed in vacuo to give the title compound (1.40 g, 98%) as a pale brown foam. LCMS (Method A): $R_T$=0.72 min, m/z=308 [M+H]$^+$.

Step 2: tert-Butyl 4-(4-((6-(2,6-dichlorophenyl)-5-oxo-5,6-dihydropyrido[4,3-d]pyrimidin-2-yl)amino)-2-(hydroxymethyl)phenyl)piperazine-1-carboxylate: mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 20 min, DIPEA (0.155 mL, 0.887 mmol) and tert-butyl 4-(4-amino-2-(hydroxymethyl)phenyl)piperazine-1-carboxylate (100 mg, 0.325 mmol) were added, successively, and the temperature was increased to 60° C. After 16 h, the reaction mixture was allowed to cool and loaded directly onto a KP-NH column and purified by flash chromatography (0-100%, EtOAc in cyclohexane). The pure fractions were concentrated to give the title compound (59.7 mg, 34%) as a pale yellow solid. LCMS (Method A): $R_T$=1.42 min, m/z=597, 599 [M+H]$^+$.

Step 3: 6-(2,6-Dichlorophenyl)-2-((3-(hydroxymethyl)-4-(piperazin-1-yl)phenyl)amino)pyrido[4,3-d]pyrimidin-5(6H)-one: TFA (2.0 mL, 26.0 mmol) was added to a stirred solution of tert-butyl 4-(4-((6-(2,6-dichlorophenyl)-5-oxo-5,6-dihydropyrido[4,3-d]pyrimidin-2-yl)amino)-2-(hydroxymethyl)phenyl)piperazine-1-carboxylate (59.7 mg, 0.100 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography using a KP-NH column (0-100% EtOAc in cyclohexane) to give material that required further purification by preparative HPLC. The pure fractions were concentrated to give the title compound (14.5 mg, 29%) as a yellow solid. LCMS (Method A): $R_T$=0.75 min, m/z=497, 498 [M+H]$^+$. $^1$H NMR (500 MHz, methanol-d4): δ 9.22 (s, 1H), 7.82 (br s, 1H), 7.72 (br d, 1H), 7.64 (d, 2H), 7.53 (dd, 1H), 7.49 (d, 1H), 7.18 (d, 1H), 6.64 (d, 1H), 4.77 (s, 2H, overlapping solvent), 2.99 (t, 4H), 2.91 (t, 4H).

Example 19

6-(2,6-Dichlorophenyl)-2-((4-morpholinophenyl)amino)pyrido[4,3-d]pyrimidin-5(6H)-one

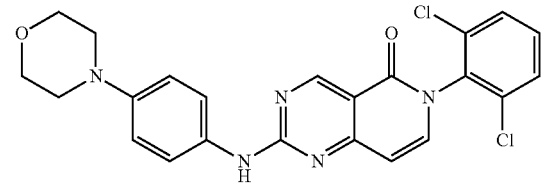 [SMILES: O=c1c2cnc(Nc3ccc(N4CCOCC4)cc3)nc2ccn1-c1c(Cl)cccc1Cl]

mCPBA (<77% pure) (102 mg, assumed 0.455 mmol) in DCM (0.5 mL) was added to a stirred solution of -(2,6-dichlorophenyl)-2-(methylthio)pyrido[4,3-d]pyrimidin-5(6H)-one (100 mg, 0.296 mmol) in toluene (3.0 mL) at RT under nitrogen. After 1 h, DIPEA (0.155 mL, 0.887 mmol) and 4-morpholinoaniline (52.7 mg, 0.296 mmol) [commercially available] were added, successively, and the temperature was increased to 60° C. After 20 h, the reaction mixture was cooled and loaded directly onto a KP-NH column and purified by flash chromatography (0-100%, EtOAc in cyclohexane) to give the title compound (49.1 mg, 35%) as a yellow solid. LCMS (Method A): $R_T$=1.23 min, m/z=468, 470 [M+H]$^+$. $^1$H NMR (500 MHz, methanol-d4): δ 9.19 (s, 1H), 7.71-7.61 (m, 4H), 7.52 (dd, 1H), 7.47 (d, 1H), 7.03-6.99 (m, 2H), 6.59 (d, 1H), 3.85 (t, 4H), 3.14 (t, 4H).

Example 20

6-(2,6-Dichlorophenyl)-2-((3-((methylamino)methyl)-4-morpholinophenyl)amino)pyrido[4,3-d]pyrimidin-5(6H)-one

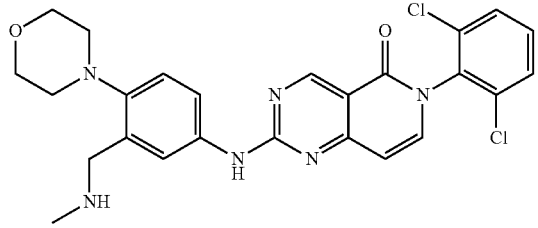 [SMILES: CNCc1cc(Nc2ncc3c(=O)n(-c4c(Cl)cccc4Cl)ccc3n2)ccc1N1CCOCC1]

Step 1: 2-Morpholino-5-nitrobenzaldehyde: To a solution of 2-chloro-5-nitrobenzaldehyde (3.00 g, 16.2 mmol) in DMF (20 mL) was added DIPEA (4.24 mL, 24.3 mmol) and morpholine (1.55 g, 17.8 mmol). The reaction mixture was stirred at 90° C. for 4 h. The reaction was cooled to RT and water was added. The mixture was extracted with EtOAc. The organic layer was washed with brine, dried over Na$_2$SO$_4$, filtered, and the solvents were removed in vacuo to give the title compound (crude 3.2 g, 85%), which was used in the next step without further purification. LCMS (Method A): $R_T$=0.99 min, m/z=237 [M+H]$^+$.

Step 2: N-Methyl-1-(2-morpholino-5-nitrophenyl)methanamine: To a suspension of sodium bicarbonate (0.356 g, 4.23 mmol) in MeOH (6 mL) was added 2-morpholino-5-nitrobenzaldehyde (0.5 g, 2.12 mmol) and methylamine (2M in MeOH) (1.27 mL, 2.54 mmol). The reaction mixture was stirred at 70° C. After 4 h, the reaction was cooled to 0° C. and sodium borohydride (0.096 g, 2.54 mmol) was added. The reaction was stirred at RT for 2 h. A few drops of water were added and the solvents were removed in vacuo. The remaining residue was partitioned between DCM and brine, separated, extracted using further DCM, dried over Na$_2$SO$_4$, filtered, and the solvents were removed in vacuo to give the title compound (crude, 450 mg, 85%), which was used in the next step without further purification. LCMS (Method A): $R_T$=0.47 min, m/z=221 [M+H-30 (CH$_3$NH)]$^+$.

Step 3: tert-Butyl methyl(2-morpholino-5-nitrobenzyl)carbamate: To a solution of N-methyl-1-(2-morpholino-5-nitrophenyl)methanamine (450 mg, 1.79 mmol) in THF (5 mL) was added triethylamine (0.50 mL, 3.58 mmol) and Boc$_2$O (0.46 mL, 1.97 mmol). The reaction mixture was stirred at room temperature for 16 h. Water was added and the reaction mixture was extracted using EtOAc. The combined organic phase was washed using water and brine, dried over Na$_2$SO$_4$, filtered, and the solvents were removed in vacuo to give the title compound (crude, 622 mg, 99%), which was used in the next step without further purification. LCMS (Method A): $R_T$=1.39 min, m/z=296 [M+H-56 ($^t$Bu)]$^+$.

Step 4: tert-Butyl 5-amino-2-morpholinobenzyl(methyl)carbamate: To a solution of tert-butyl methyl(2-morpholino-5-nitrobenzyl)carbamate (640 mg, 1.82 mmol) in ethanol (4 mL) was added 10% palladium on carbon (194 mg, 0.182 mmol) and ammonium formate (230 mg, 3.64 mmol). The reaction mixture was stirred at 60° C. for 3 h. The mixture was filtered through Celite® and filtrate was concentrated in vacuo. The remaining residue was partitioned between EtOAc and satd sodium bicarbonate (aq) solution, separated, the organic phase was washed using brine, dried over Na$_2$SO$_4$, filtered, and the solvents were removed in vacuo to give the title compound (crude, 580 mg, 99%), which was used in the next step without further purification. LCMS (Method A): $R_T$=0.83 min, m/z=322 [M+H]$^+$.

Step 5: tert-Butyl 5-((6-(2,6-dichlorophenyl)-5-oxo-5,6-dihydropyrido[4,3-d]pyrimidin-2-yl)amino)-2-morpholinobenzyl(methyl)carbamate: mCPBA (<77% pure) (102 mg, assumed 0.455 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 20 min, DIPEA (0.155 mL, 0.887 mmol) and tert-butyl 5-amino-2-morpholinobenzyl(methyl)carbamate (95 mg, 0.296 mmol) in DMF (0.5 mL) were added, successively, and the temperature was increased to 60° C. After 16 h, the reaction mixture was cooled and loaded directly onto a KP-NH column and purified by flash chromatography (0-50%, EtOAc in cyclohexane) to give the title compound (32.7 mg, 18%) as a pale yellow solid. LCMS (Method A): $R_T$=1.55 min, m/z=611, 613 [M+H]$^+$.

Step 6: 6-(2,6-Dichlorophenyl)-2-((3-((methylamino)methyl)-4-morpholinophenyl)amino)pyrido[4,3-d]pyrimidin-5(6H)-one: TFA (2.0 mL, 26.0 mmol) was added to a stirred solution of tert-butyl 5-((6-(2,6-dichlorophenyl)-5-oxo-5,6-dihydropyrido[4,3-d]pyrimidin-2-yl)amino)-2-morpholinobenzyl(methyl)carbamate (32.7 mg, 0.053 mmol) in DCM (2.0 mL) at RT under nitrogen. After 2 h, due to incomplete reaction, further TFA (2.0 mL, 26.0 mmol) was added. After 6 h, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography (0-100%, EtOAc in cyclohexane; then 0-5% MeOH in EtOAc) to give the title compound (16.2 mg, 58%) as a pale yellow solid. LCMS (Method A): $R_T$=0.84 min, m/z=511, 513 [M+H]$^+$. $^1$H NMR (500 MHz, methanol-d4): δ 9.22 (s, 1H), 7.77 (br d, 1H), 7.70 (d, 1H), 7.64 (d, 2H), 7.53 (dd, 1H), 7.50 (d, 1H), 7.26 (d, 1H), 6.64 (d, 1H), 3.87 (s, 2H), 3.85 (t, 4H), 2.93 (t, 4H), 2.45 (s, 3H).

Example 21

6-(2,6-Dichlorophenyl)-2-((4-(4-(2-hydroxyethyl)piperazin-1-yl)phenyl)amino)pyrido[4,3-d]pyrimidin-5(6H)-one

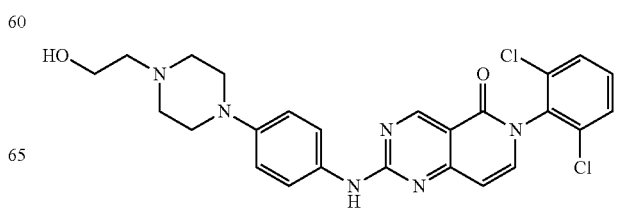

mCPBA (<77% pure) (102 mg, assumed 0.455 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, DIPEA (0.155 mL, 0.887 mmol) and 2-(4-(4-aminophenyl)piperazin-1-yl)ethanol (65.4 mg, 0.296 mmol) [commercially available] were added, successively, and the temperature was increased to 60° C. After 16 h, the reaction mixture was cooled and loaded directly onto a KP-NH column and purified by flash chromatography (0-100%, EtOAc in cyclohexane) to give material that required further purification by preparative HPLC. The pure fractions were concentrated to give the title compound (39.8 mg, 26%) as a yellow solid. LCMS (Method A): $R_T$=0.80 min, m/z=511, 513 [M+H]$^+$. $^1$H NMR (500 MHz, methanol-d4): δ 9.19 (s, 1H), 7.70-7.60 (m, 4H), 7.52 (dd, 1H), 7.47 (d, 1H), 7.02 (d, 2H), 6.60 (d, 1H), 3.75 (t, 2H), 3.23 (t, 4H), 2.77 (m, 4H), 2.66 (t, 2H).

Example 22

8-(3-Aminoprop-1-yn-1-yl)-6-(2,6-dichlorophenyl)-2-((4-morpholinophenyl)amino)pyrido[4,3-d]pyrimidin-5(6H)-one

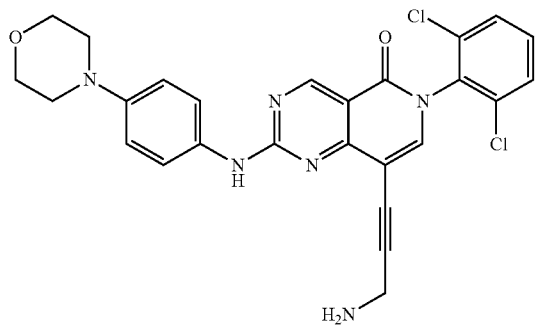 [SMILES: NCC#Cc1cn(-c2c(Cl)cccc2Cl)c(=O)c2cnc(Nc3ccc(N4CCOCC4)cc3)nc12]

Step 1: tert-Butyl (3-(6-(2,6-dichlorophenyl)-2-(methylthio)-5-oxo-5,6-dihydropyrido[4,3-d]pyrimidin-8-yl)prop-2-yn-1-yl)carbamate: Copper(I) iodide (0.6 mg, 3.0 μmol) and bis(triphenylphosphine)palladium(II) chloride (4.2 mg, 6.0 μmol) were added to a pre-degassed solution of 8-bromo-6-(2,6-dichlorophenyl)-2-(methylthio)pyrido[4,3-d]pyrimidin-5(6H)-one (50 mg, 0.120 mmol), tert-butyl prop-2-yn-1-ylcarbamate (37.2 mg, 0.240 mmol) and tetrabutylammonium iodide (89 mg, 0.240 mmol) in triethylamine (0.2 ml, 1.435 mmol)/DMF (1.0 mL) in a 10 mL vial. The reaction vessel was sealed and heated under microwave conditions (CEM Explorer/Discover) at 100° C. (80 W ceiling) for 15 min. Due to incomplete conversion, the reaction was rerun at 100° C. (80 W ceiling) for a further 45 min. The reaction mixture was partitioned between diethyl ether and 1:1, water/brine, separated, extracted (diethyl ether×3), dried (Phase Separator), the solvents were removed in vacuo, and the remaining residue was purified by flash chromatography (0-100%, EtOAc in cyclohexane) to give the title compound (45.4 mg, 77%) as a pale yellow solid. LCMS (Method A): $R_T$=1.50 min, m/z=491, 493 [M+H]$^+$.

Step 2: tert-Butyl (3-(6-(2,6-dichlorophenyl)-2-((4-morpholinophenyl)amino)-5-oxo-5,6-dihydropyrido[4,3-d]pyrimidin-8-yl)prop-2-yn-1-yl)carbamate: mCPBA (<77% pure) (31.9 mg, assumed 0.142 mmol) in DCM (0.5 mL) was added to a stirred solution of tert-butyl (3-(6-(2,6-dichlorophenyl)-2-(methylthio)-5-oxo-5,6-dihydropyrido[4,3-d]pyrimidin-8-yl)prop-2-yn-1-yl)carbamate (45.4 mg, 0.092 mmol) in toluene (2.0 mL) at RT under nitrogen. After 20 min, DIPEA (0.048 mL, 0.277 mmol) and 4-morpholinoaniline (16.47 mg, 0.092 mmol) [commercially available] were added, successively, and the temperature was increased to 60° C. After 16 h, the reaction mixture was cooled and loaded directly onto a KP-NH column and purified by flash chromatography (0-50%, EtOAc in cyclohexane) to give the title compound (19.8 mg, 35%) as a yellow oil. LCMS (Method A): $R_T$=1.45 min, m/z=621, 623 [M+H]$^+$.

Step 3: 8-(3-Aminoprop-1-yn-1-yl)-6-(2,6-dichlorophenyl)-2-((4-morpholinophenyl)amino)pyrido[4,3-d]pyrimidin-5(6H)-one: TFA (2.0 mL, 26.0 mmol) was added to a stirred solution of tert-butyl (3-(6-(2,6-dichlorophenyl)-2-((4-morpholinophenyl)amino)-5-oxo-5,6-dihydropyrido[4,3-d]pyrimidin-8-yl)prop-2-yn-1-yl)carbamate (45.4 mg, 0.073 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the residue was purified by flash chromatography using a KP-NH column (0-100%, EtOAc in cyclohexane) to give the title compound (12.0 mg, 31%) as a yellow solid. LCMS (Method A): $R_T$=0.83 min, m/z=521, 523 [M+H]$^+$. $^1$H NMR (500 MHz, methanol-d4): δ 9.18 (s, 1H), 7.91 (br s, 2H), 7.83 (s, 1H), 7.65 (d, 2H), 7.54 (dd, 1H), 7.04-6.99 (m, 2H), 3.85 (t, 4H), 3.80 (s, 2H), 3.14 (t, 4H).

Example 23

6-(2,6-Dichlorophenyl)-2-((4-(piperazin-1-yl)phenyl)amino)-8-(pyridin-3-yl)pyrido[4,3-d]pyrimidin-5(6H)-one

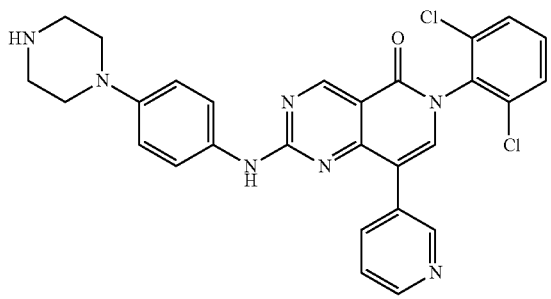 [SMILES: O=c1c2cnc(Nc3ccc(N4CCNCC4)cc3)nc2c(-c2cccnc2)cn1-c1c(Cl)cccc1Cl]

Step 1: 6-(2,6-Dichlorophenyl)-2-(methylthio)-8-(pyridin-3-yl)pyrido[4,3-d]pyrimidin-5(6H)-one: PdCl$_2$(d$_{ppf}$).DCM (2.9 mg, 3.6 μmol) was added to a pre-degassed solution of 8-bromo-6-(2,6-dichlorophenyl)-2-(methylthio)pyrido[4,3-d]pyrimidin-5(6H)-one (30 mg, 0.072 mmol), pyridin-3-ylboronic acid (13.3 mg, 0.108 mmol) and cesium carbonate (70.3 mg, 0.216 mmol) in 1,4-dioxane (1.8 mL)/water (0.2 mL) in a 10 mL vial. The vessel was sealed and irradiated at 120° C. for 20 min (CEM Discover/Explorer24). Due to incomplete conversion, the reaction was rerun under the same conditions. The reaction mixture was concentrated in vacuo to remove the 1,4-dioxane, followed by partitioning between DCM and saturated sodium bicarbonate (aq) solution. The layers were separated, aqueous phase was extracted (DCM×2), the combined organic phase was dried (Phase Separator), the solvents were removed in vacuo, and the remaining residue was purified by flash chromatography (0-100%, EtOAc in cyclohexane) to give the title compound (25.0 mg, 84%) as a pale yellow solid. LCMS (Method A): $R_T$=1.12 min, m/z=415, 417 [M+H]$^+$.

Step 2: tert-Butyl 4-(4-((6-(2,6-dichlorophenyl)-5-oxo-8-(pyridin-3-yl)-5,6-dihydropyrido[4,3-d]pyrimidin-2-yl)amino)phenyl)piperazine-1-carboxylate: mCPBA (<77% pure) (15.6 mg, assumed 0.0693 mmol) in DCM (0.5 mL) was added to a stirred solution of 6-(2,6-dichlorophenyl)-2-(methylthio)-8-(pyridin-3-yl)pyrido[4,3-d]pyrimidin-5 (6H)-one (25.0 mg, 0.060 mmol) in toluene (2.0 mL) at RT under nitrogen. After 15 min, DIPEA (0.032 mL, 0.181 mmol) and tert-butyl 4-(4-aminophenyl)piperazine-1-carboxylate (16.7 mg, 0.060 mmol) [commercially available] were added, successively, and the temperature was increased to 60° C. After 16 h, the reaction mixture was cooled and loaded directly onto a KP-NH column and purified by flash chromatography (0-100%, EtOAc in cyclohexane) to give the title compound (15.5 mg, 40%) as a yellow solid. LCMS (Method A): $R_T$=1.40 min, m/z=644, 646 [M+H]$^+$.

Step 3: 6-(2,6-Dichlorophenyl)-2-((4-(piperazin-1-yl)phenyl)amino)-8-(pyridin-3-yl)pyrido[4,3-d]pyrimidin-5 (6H)-one: TFA (1.0 mL, 12.98 mmol) was added to a stirred solution of tert-butyl 4-(4-((6-(2,6-dichlorophenyl)-5-oxo-8-(pyridin-3-yl)-5,6-dihydropyrido[4,3-d]pyrimidin-2-yl)amino)phenyl)piperazine-1-carboxylate (5.8 mg, 9.0 µmol) in DCM (1.0 mL) at RT under nitrogen. After 1 h, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography using a KP-NH column (0-100% EtOAc in cyclohexane; then 10% MeOH in EtOAc) to give the title compound (4.5 mg, 92%) as a yellow solid. LCMS (Method A): $R_T$=0.76 min, m/z=544, 546 [M+H]$^+$.

$^1$H NMR (500 MHz, methanol-d4): δ 9.28 (s, 1H), 8.84 (d, 1H), 8.56 (d, 1H), 8.14 (dt, 1H), 7.82 (s, 1H), 7.66 (d, 2H), 7.60-7.51 (m, 4H), 6.92 (br d, 2H), 3.24 (br d, 4H), 3.19 (br d, 4H).

Example 24

6-(2-Chlorophenyl)-2-((3-methyl-4-(piperazin-1-yl)phenyl)amino)pyrido[4,3-d]pyrimidin-5(6H)-one

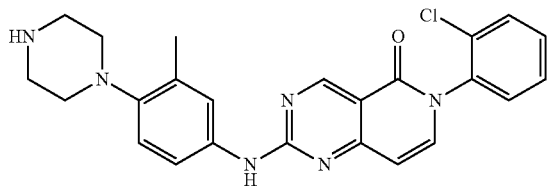 [SMILES: Cc1cc(Nc2ncc3c(=O)n(-c4ccccc4Cl)ccc3n2)ccc1N1CCNCC1]

Step 1: N-(2-Chlorophenyl)-4-methyl-2-(methylthio)pyrimidine-5-carboxamide: phosphorus trichloride (0.237 mL, 2.71 mmol) was added to a stirred solution of 4-methyl-2-(methylthio)pyrimidine-5-carboxylic acid (500 mg, 2.71 mmol) and 2-chloroaniline (0.285 mL, 2.71 mmol) in chlorobenzene (10 mL) at 135° C. under nitrogen. After 1 h, the reaction mixture was allowed to cool and was partitioned between DCM and 2M sodium carbonate (aq) solution, separated, extracted (DCM×2), dried (Phase Separator), and the solvents were removed in vacuo to give the title compound (699 mg, 88%) as a yellow solid that was carried through to the next step without further purification. LCMS (Method A): $R_T$=1.21 min, m/z=294 [M+H]$^+$.

Step 2: 6-(2-Chlorophenyl)-2-(methylthio)pyrido[4,3-d]pyrimidin-5(6H)-one: DMF-DMA (0.382 mL, 2.85 mmol) was added to a stirred solution of N-(2-chlorophenyl)-4-methyl-2-(methylthio)pyrimidine-5-carboxamide (699 mg, 2.38 mmol) in DMF (7.0 mL) at RT under nitrogen. The reaction mixture was heated to 150° C. After 1 h, the reaction mixture was cooled and was partitioned using diethyl ether and 1:1 brine/water, separated, further washed with 1:1 brine/water, the organic phase was dried (Phase Separator), the solvents were removed in vacuo, and the remaining residue was purified by flash chromatography (0-100%, EtOAc in cyclohexane) to give the title compound (391 mg, 54%) as a pale yellow solid. LCMS (Method A): $R_T$=1.21 min, m/z=304 [M+H]$^+$.

Step 3: tert-Butyl 4-(4-((6-(2-chlorophenyl)-5-oxo-5,6-dihydropyrido[4,3-d]pyrimidin-2-yl)amino)-2-methylphenyl)piperazine-1-carboxylate: mCPBA (<77% pure) (85 mg, assumed 0.380 mmol) in DCM (0.5 mL) was added to a stirred solution of 6-(2-chlorophenyl)-2-(methylthio)pyrido[4,3-d]pyrimidin-5(6H)-one (100 mg, 0.329 mmol) in toluene (3.0 mL) at RT under nitrogen. After 15 min, DIPEA (0.172 mL, 0.988 mmol) and tert-butyl 4-(4-amino-2-methylphenyl)piperazine-1-carboxylate (96 mg, 0.329 mmol) [commercially available] were added, successively, and the temperature was increased to 60° C. After 16 h, the reaction mixture was cooled and loaded directly onto a KP-NH column and purified by flash chromatography (0-50%, EtOAc in cyclohexane) to give the title compound (134 mg, 75%) as a yellow solid. LCMS (Method A): $R_T$=1.63 min, m/z=547 [M+H]$^+$.

Step 4: 6-(2-Chlorophenyl)-2-((3-methyl-4-(piperazin-1-yl)phenyl)amino)pyrido[4,3-d]pyrimidin-5(6H)-one: TFA (1.0 mL, 13.0 mmol) was added to a stirred solution of tert-butyl 4-(4-((6-(2-chlorophenyl)-5-oxo-5,6-dihydropyrido[4,3-d]pyrimidin-2-yl)amino)-2-methylphenyl)piperazine-1-carboxylate (134 mg, 0.245 mmol) in DCM (1.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography using a KP-NH column (0-100% EtOAc in cyclohexane) to give the title compound (56.1 mg, 51%) as a pale yellow solid. LCMS (Method A): $R_T$=0.82 min, m/z=447 [M+H]$^+$. $^1$H NMR (500 MHz, methanol-d4): δ 9.20 (s, 1H), 7.67-7.63 (m, 1H), 7.61 (br d, 1H), 7.55-7.49 (m, 5H), 7.07 (d, 1H), 6.56 (d, 1H), 3.00 (t, 4H), 2.89 (t, 4H), 2.34 (s, 3H).

Example 25

2-((3-(Aminomethyl)phenyl)amino)-6-(2,6-dichlorophenyl)pyrido[4,3-d]pyrimidin-5(6H)-one

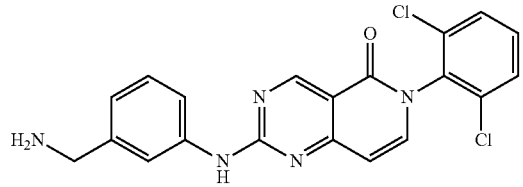 [SMILES: NCc1cccc(Nc2ncc3c(=O)n(-c4c(Cl)cccc4Cl)ccc3n2)c1]

Step 1: tert-Butyl 3-((6-(2,6-dichlorophenyl)-5-oxo-5,6-dihydropyrido[4,3-d]pyrimidin-2-yl)amino)benzylcarbamate: mCPBA (<77% pure) (102 mg, assumed 0.455 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, DIPEA (0.155 mL, 0.887 mmol) and tert-butyl 3-aminobenzylcarbamate (65.7 mg, 0.296 mmol) [commercially available] were added, successively, and the temperature was increased to 60° C. After 18 h, the reaction mixture was cooled and loaded directly onto a KP-NH column and purified by flash chromatography (0-50%, EtOAc in cyclohexane) to give the title compound (59.9 mg, 40%) as a yellow gum. LCMS (Method A): $R_T$=1.43 min, m/z=512, 514 [M+H]$^+$.

Step 2: 2-((3-(Aminomethyl)phenyl)amino)-6-(2,6-dichlorophenyl)pyrido[4,3-d]pyrimidin-5(6H)-one: TFA (2.0 mL, 26.0 mmol) was added to a stirred solution of tert-butyl 3-((6-(2,6-dichlorophenyl)-5-oxo-5,6-dihydropyrido[4,3-d]pyrimidin-2-yl)amino)benzylcarbamate (59.9 mg, 0.117 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography using a KP-NH column (0-100%, EtOAc in cyclohexane; then 10% MeOH in EtOAc) to give the title compound (33.7 mg, 70%) as a pale yellow solid. LCMS (Method A): $R_T$=0.80 min, m/z=412, 414 [M+H]$^+$. $^1$H NMR (500 MHz, methanol-d4): δ 9.24 (s, 1H), 7.77-7.71 (m, 2H), 7.66-7.62 (m, 2H), 7.53 (dd, 1H), 7.51 (d, 1H), 7.34 (t, 1H), 7.11 (br d, 1H), 6.66 (d, 1H), 3.84 (s, 2H).

Example 26

6-(2,6-Dichlorophenyl)-2-((3-(4-methylpiperazin-1-yl)phenyl)amino)pyrido[4,3-d]pyrimidin-5(6H)-one

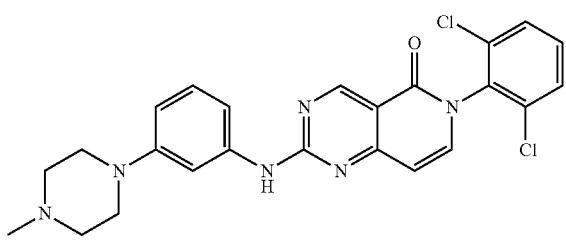 [SMILES: CN1CCN(c2cccc(Nc3ncc4c(=O)n(-c5c(Cl)cccc5Cl)ccc4n3)c2)CC1]

mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, further mCPBA (23 mg) was added. After a further 15 min, DIPEA (0.155 mL, 0.887 mmol) and 3-(4-methylpiperazin-1-yl)aniline (56.6 mg, 0.296 mmol) [commercially available] were added, successively, and the temperature was increased to 60° C. After 16 h, the reaction mixture was cooled and loaded directly onto a KP-NH column and purified by flash chromatography (0-100%, EtOAc in cyclohexane) to give the title compound (41.8 mg, 29%) as a pale yellow solid. LCMS (Method A): $R_T$=0.84 min, m/z=481, 483 [M+H]$^+$. $^1$H NMR (500 MHz, CDCl$_3$): δ 9.35 (s, 1H), 7.53-7.42 (m, 4H), 7.38 (dd, 1H), 7.17-7.11 (m, 2H), 6.71 (dd, 1H), 6.53 (d, 1H), 3.31 (br s, 4H), 2.67 (br s, 4H), 2.42 (s, 3H).

Example 27

2-((3-Chloro-4-(piperazin-1-yl)phenyl)amino)-6-(2,6-dichlorophenyl)pyrido[4,3-d]pyrimidin-5(6H)-one

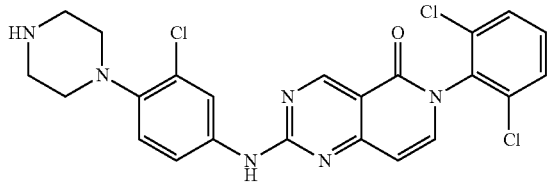 [SMILES: O=c1c2cnc(Nc3ccc(N4CCNCC4)c(Cl)c3)nc2ccn1-c1c(Cl)cccc1Cl]

Step 1: tert-Butyl 4-(2-chloro-4-((6-(2,6-dichlorophenyl)-5-oxo-5,6-dihydropyrido[4,3-d]pyrimidin-2-yl)amino)phenyl)piperazine-1-carboxylate: mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 20 min, DIPEA (0.155 mL, 0.887 mmol) and tert-butyl 4-(4-amino-2-chlorophenyl)piperazine-1-carboxylate (92 mg, 0.296 mmol) [commercially available] were added, successively, and the temperature was increased to 60° C. After 18 h, the reaction mixture was cooled and loaded directly onto a KP-NH column and purified by flash chromatography (0-50%, EtOAc in cyclohexane) to give the title compound (125 mg, 70%) as a pale yellow solid. LCMS (Method A): $R_T$=1.71 min, m/z=601, 603 [M+H]$^+$.

Step 2: 2-((3-Chloro-4-(piperazin-1-yl)phenyl)amino)-6-(2,6-dichlorophenyl)pyrido[4,3-d]pyrimidin-5(6H)-one: TFA (2.0 mL, 26.0 mmol) was added to a stirred solution of tert-butyl 4-(2-chloro-4-((6-(2,6-dichlorophenyl)-5-oxo-5,6-dihydropyrido[4,3-d]pyrimidin-2-yl)amino)phenyl)piperazine-1-carboxylate (125 mg, 0.207 mmol) in DCM (2.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), the solvents were removed in vacuo, and the remaining residue was purified by flash chromatography using a KP-NH column (0-100% EtOAc in cyclohexane) to give the title compound (9.4 mg, 9%) as a pale yellow solid. LCMS (Method A): $R_T$=0.88 min, m/z=501, 503 [M+H]$^+$. $^1$H NMR (500 MHz, methanol-d4): δ 9.24 (s, 1H), 7.98 (s, 1H), 7.70-7.60 (m, 3H), 7.53 (dd, 1H), 7.51 (d, 1H), 7.14 (d, 1H), 6.64 (d, 1H), 3.01 (s, 8H).

Example 28

N-(6-(2,6-Dichlorophenyl)-5-oxo-2-((4-(piperazin-1-yl)phenyl)amino)-5,6-dihydropyrido[4,3-d]pyrimidin-8-yl)acetamide

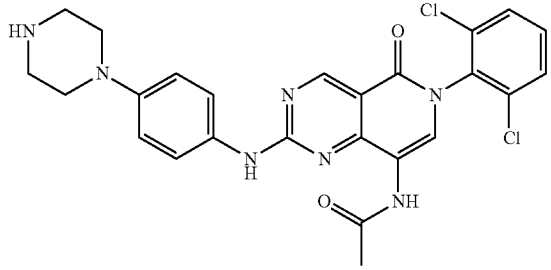 [SMILES: CC(=O)Nc1cn(-c2c(Cl)cccc2Cl)c(=O)c2cnc(Nc3ccc(N4CCNCC4)cc3)nc12]

Step 1: N-(6-(2,6-Dichlorophenyl)-2-(methylthio)-5-oxo-5,6-dihydropyrido[4,3-d]pyrimidin-8-yl)acetamide: Pd2(dba)3 (2.2 mg, 2.4 μmol) was added to a pre-degassed stirred solution of 8-bromo-6-(2,6-dichlorophenyl)-2-(methylthio)pyrido[4,3-d]pyrimidin-5(6H)-one (50 mg, 0.120 mmol), acetamide (10.6 mg, 0.180 mmol), Xantphos (1.4 mg, 2.4 μmol) and cesium carbonate (78 mg, 0.240 mmol) in 1,4-dioxane (1.0 mL) at RT in a 10 mL vial. The vessel was sealed and heated to 100° C. After 2 h, the solvents were removed in vacuo and the remaining residue was partitioned between DCM and water, separated, extracted (DCM×2), and dried (Phase Separator). The solvents were removed in vacuo and the remaining residue was purified by flash chromatography (0-100%, EtOAc in cyclohexane) to give the title compound (8.0 mg, 17%) as a white solid. LCMS (Method A): $R_T$=1.13 min, m/z=395, 397 [M+H]$^+$.

Step 2: tert-Butyl 4-(4-((8-acetamido-6-(2,6-dichlorophenyl)-5-oxo-5,6-dihydropyrido[4,3-d]pyrimidin-2-yl)amino)phenyl)piperazine-1-carboxylate: mCPBA (<77% pure) (5.24 mg, assumed 0.023 mmol) in DCM (0.5 mL) was added to a stirred solution of N-(6-(2,6-dichlorophenyl)-2-(methylthio)-5-oxo-5,6-dihydropyrido[4,3-d]pyrimidin-8-yl)acetamide (8.0 mg, 0.020 mmol) in toluene (1.0 mL) at RT under nitrogen. After 30 min, DIPEA (10.6 μL, 0.061 mmol) and tert-butyl 4-(4-aminophenyl)piperazine-1-carboxylate (6.2 mg, 0.022 mmol) [commercially available] in toluene (0.5 mL) were added, successively, and the temperature was increased to 60° C. After 16 h, the reaction mixture was allowed to cool to RT, and was loaded onto a KP-NH column and purified by flash chromatography (0-100%, EtOAc in cyclohexane) to give the title compound (3.7 mg, 29%) as a yellow solid. LCMS (Method A): $R_T$=1.39 min, m/z=624, 626 [M+H]$^+$.

Step 3: N-(6-(2,6-Dichlorophenyl)-5-oxo-2-((4-(piperazin-1-yl)phenyl)amino)-5,6-dihydropyrido[4,3-d]pyrimidin-8-yl)acetamide: TFA (1.0 mL, 13.0 mmol) was added to a stirred solution of tert-butyl 4-(4-((8-acetamido-6-(2,6-dichlorophenyl)-5-oxo-5,6-dihydropyrido[4,3-d]pyrimidin-2-yl)amino)phenyl)piperazine-1-carboxylate (3.7 mg, 5.9 μmol) in DCM (1.0 mL) at RT under nitrogen. After 30 min, the solvents were removed in vacuo and the remaining residue was partitioned between DCM and satd sodium bicarbonate (aq) solution, separated, extracted (DCM×2), dried (Phase Separator), and the solvents were removed in vacuo. The remaining residue was purified by flash chromatography using a KP-NH column (0-100%, EtOAc in cyclohexane; then 10% MeOH in EtOAc) to give the title compound (1.1 mg, 32%) as a yellow solid. LCMS (Method A): $R_T$=0.82 min, m/z=524, 526 [M+H]$^+$.

Example 29

6-(2,6-Dichlorophenyl)-2-((3-fluoro-4-(piperazin-1-yl)phenyl)amino)pyrido[4,3-d]pyrimidin-5(6H)-one

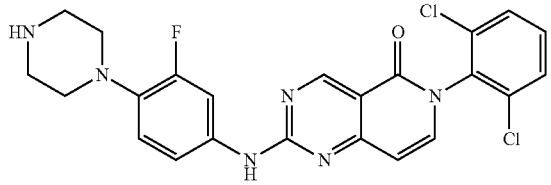 [SMILES: O=c1c2cnc(Nc3ccc(N4CCNCC4)c(F)c3)nc2ccn1-c1c(Cl)cccc1Cl]

Step 1: tert-Butyl 4-(4-((6-(2,6-dichlorophenyl)-5-oxo-5,6-dihydropyrido[4,3-d]pyrimidin-2-yl)amino)-2-fluorophenyl)piperazine-1-carboxylate: mCPBA (<77% pure) (78 mg, assumed 0.348 mmol) in DCM (0.5 mL) was added to a stirred solution of 6-(2,6-dichlorophenyl)-2-(methylthio)pyrido[4,3-d]pyrimidin-5(6H)-one (102 mg, 0.302 mmol) in toluene (3.0 mL) at RT under nitrogen. After 15 min, DIPEA (0.158 mL, 0.905 mmol) and tert-butyl 4-(4-amino-2-fluorophenyl)piperazine-1-carboxylate (89 mg, 0.302 mmol) [commercially available] were added, successively, and the temperature was increased to 60° C. After 16 h, the reaction mixture was cooled and loaded directly onto a KP-NH column and purified by flash chromatography (0-50%, EtOAc in cyclohexane) to give the title compound (85.8 mg, 49%) as a yellow solid. LCMS (Method A): $R_T$=1.63 min, m/z=585, 587 [M+H]$^+$.

Step 2: 6-(2,6-Dichlorophenyl)-2-((3-fluoro-4-(piperazin-1-yl)phenyl)amino)pyrido[4,3-d]pyrimidin-5(6H)-one: TFA (2.0 mL, 26.0 mmol) was added to a stirred solution of tert-butyl 4-(4-((6-(2,6-dichlorophenyl)-5-oxo-5,6-dihydropyrido[4,3-d]pyrimidin-2-yl)amino)-2-fluorophenyl)piperazine-1-carboxylate (85.8 mg, 0.147 mmol) in DCM (2.0 mL) at RT under nitrogen. After 30 min, the solvents were removed in vacuo and the remaining residue was partitioned between DCM and saturated sodium bicarbonate (aq) solution, separated, extracted (DCM×2), dried (Phase Separator), the solvents were removed in vacuo to give the title compound (66.6 mg, 91%) as a yellow solid. LCMS (Method A): $R_T$=0.86 min, m/z=485, 487 [M+H]$^+$. $^1$H NMR (500 MHz, methanol-d4): δ 9.23 (s, 1H), 7.80 (br d, 1H), 7.66-7.62 (m, 2H), 7.53 (dd, 1H), 7.51 (d, 1H), 7.43 (br d, 1H), 7.05 (t, 1H), 6.65 (d, 1H), 3.09-2.99 (m, 8H).

Example 30

6-(2,6-Dichlorophenyl)-2-((3,5-difluoro-4-(piperazin-1-yl)phenyl)amino)pyrido[4,3-d]pyrimidin-5(6H)-one

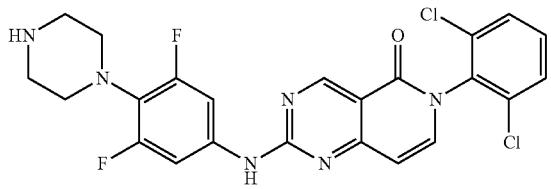 [SMILES: O=c1c2cnc(Nc3cc(F)c(N4CCNCC4)c(F)c3)nc2ccn1-c1c(Cl)cccc1Cl]

Step 1: tert-Butyl 4-(4-((6-(2,6-dichlorophenyl)-5-oxo-5,6-dihydropyrido[4,3-d]pyrimidin-2-yl)amino)-2,6-difluorophenyl)piperazine-1-carboxylate: mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, DIPEA (0.155 mL, 0.887 mmol) and tert-butyl 4-(4-amino-2,6-difluorophenyl)piperazine-1-carboxylate (93 mg, 0.296 mmol) [commercially available] were added, successively, and the temperature was increased to 60° C. After 16 h, the reaction mixture was cooled and loaded directly onto a KP-NH column and purified by flash chromatography (0-50%, EtOAc in cyclohexane). The pure fractions were concentrated to give the title compound (19.6 mg, 11%) as a yellow solid. LCMS (Method A): $R_T$=1.71 min, m/z=603, 605 [M+H]$^+$.

Step 2: 6-(2,6-Dichlorophenyl)-2-((3,5-difluoro-4-(piperazin-1-yl)phenyl)amino)pyrido[4,3-d]pyrimidin-5(6H)-one: TFA (2.0 mL, 26.0 mmol) was added to a stirred solution of tert-butyl 4-(4-((6-(2,6-dichlorophenyl)-5-oxo-5,6-dihydropyrido[4,3-d]pyrimidin-2-yl)amino)-2,6-difluorophenyl)

piperazine-1-carboxylate (19.6 mg, 0.032 mmol) in DCM (2.0 mL) at RT under nitrogen. After 30 min, the solvents were removed in vacuo and the remaining residue was partitioned between DCM and saturated sodium bicarbonate (aq) solution, separated, extracted (DCM×2), dried (Phase Separator), the solvents were removed in vacuo, and the material was purified by flash chromatography using a KP-NH column (0-100%, EtOAc in cyclohexane) to give the title compound (7.8 mg, 48%) as an off-white solid. LCMS (Method A): $R_T$=0.89 min, m/z=503, 505 [M+H]$^+$. $^1$H NMR (500 MHz, methanol-d4): δ 9.27 (s, 1H), 7.66-7.62 (m, 2H), 7.57-7.49 (m, 4H), 6.69 (d, 1H), 3.15 (t, 4H), 2.95 (t, 4H).

Example 31

6-(2,6-Dichlorophenyl)-2-((6-(4-methylpiperazin-1-yl)pyridin-3-yl)amino)pyrido[4,3-d]pyrimidin-5(6H)-one

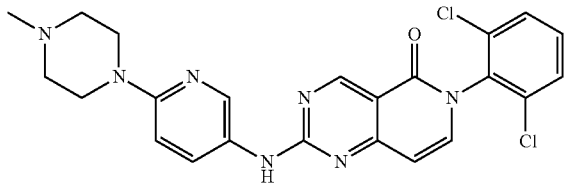

mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 15 min, DIPEA (0.155 mL, 0.887 mmol) and 6-(4-methylpiperazin-1-yl)pyridin-3-amine (56.8 mg, 0.296 mmol) [commercially available] were added, successively, and the temperature was increased to 60° C. After 16 h, the reaction mixture was cooled and loaded directly onto a KP-NH column and purified by flash chromatography (0-50%, EtOAc in cyclohexane). The pure fractions were concentrated to give the title compound (31.1 mg, 22%) as a yellow solid. LCMS (Method A): $R_T$=0.76 min, m/z=482, 484 [M+H]$^+$. $^1$H NMR (500 MHz, methanol-d4): δ 9.20 (s, 1H), 8.50 (br s, 1H), 8.01 (br d, 1H), 7.65-7.61 (m, 2H), 7.52 (dd, 1H), 7.49 (d, 1H), 6.89 (d, 1H), 6.59 (d, 1H), 3.54 (t, 4H), 2.59 (t, 4H), 2.36 (s, 3H).

Example 32

6-(2,6-Dichlorophenyl)-2-((4-(4-methylpiperazine-1-carbonyl)phenyl)amino)pyrido[4,3-d]pyrimidin-5(6H)-one

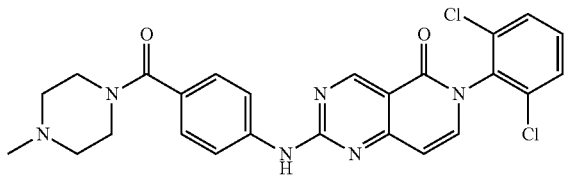 [SMILES: CN1CCN(C(=O)c2ccc(Nc3ncc4c(=O)n(-c5c(Cl)cccc5Cl)ccc4n3)cc2)CC1]

mCPBA (<77% pure) (77 mg, assumed 0.342 mmol) in DCM (0.5 mL) was added to a stirred solution of 6-(2,6-dichlorophenyl)-2-(methylthio)pyrido[4,3-d]pyrimidin-5(6H)-one (100 mg, 0.296 mmol) in toluene (3.0 mL) at RT under nitrogen. After 30 min, DIPEA (0.155 mL, 0.887 mmol) and (4-aminophenyl)(4-methylpiperazin-1-yl)methanone (64.8 mg, 0.296 mmol) [commercially available] were added, successively and the temperature was increased to 60° C. After 16 h, the reaction mixture was cooled and loaded directly onto a KP-NH column and purified by flash chromatography (0-100%, EtOAc in cyclohexane). The resultant material required re-purification by flash chromatography on a KP-Sil column (0-10%, MeOH in EtOAc). The resultant material required re-purification by preparative HPLC. The pure fractions were concentrated and the resultant material was freeze-dried to give the title compound (10.2 mg, 7%) as a white solid. LCMS (Method A): $R_T$=0.79 min, m/z=509, 511 [M+H]$^+$. $^1$H NMR (500 MHz, methanol-d4): δ 9.28 (s, 1H), 7.98 (d, 2H), 7.66-7.62 (m, 2H), 7.56-7.51 (m, 2H), 7.48-7.43 (m, 2H), 6.69 (d, 1H), 3.68 (br s, 4H), 2.49 (br s, 4H), 2.34 (s, 3H).

Example 33

2-(4-(4-((6-(2,6-Dichlorophenyl)-5-oxo-5,6-dihydropyrido[4,3-d]pyrimidin-2-yl)amino)phenyl)piperazin-1-yl)acetic acid

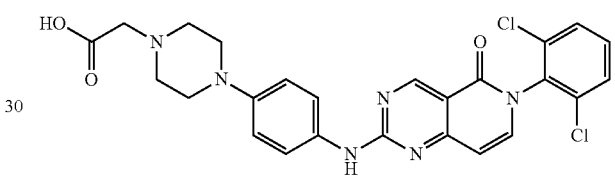

Step 1: Ethyl 2-(4-(4-((6-(2,6-dichlorophenyl)-5-oxo-5,6-dihydropyrido[4,3-d]pyrimidin-2-yl)amino)phenyl)piperazin-1-yl)acetate: Ethyl bromoacetate (0.024 mL, 0.217 mmol) was added to a stirred solution of 6-(2,6-dichlorophenyl)-2-((4-(piperazin-1-yl)phenyl)amino)pyrido[4,3-d]pyrimidin-5(6H)-one (67.7 mg, 0.145 mmol) and triethylamine (0.061 mL, 0.435 mmol) in DCM (2.0 mL) at 0° C. under nitrogen. After 1 h, the temperature was allowed to increase to RT. After 2 h, due to incomplete reaction, further triethylamine (30 µL) and ethyl bromoacetate (12 µL) were added. After a further 2 h, due to incomplete reaction, further triethylamine (30 µL) and ethyl bromoacetate (12 µL) were added. After a further 16 h, the solvents were removed in vacuo and the remaining residue was purified by flash chromatography using a KP-NH column (0-50%, EtOAc in cyclohexane) to give the title compound (68.7 mg, 86%) as a pale yellow solid. LCMS (Method A): $R_T$=0.94 min, m/z=553, 555 [M+H]$^+$.

Step 2: 2-(4-(4-((6-(2,6-Dichlorophenyl)-5-oxo-5,6-dihydropyrido[4,3-d]pyrimidin-2-yl)amino)phenyl)piperazin-1-yl)acetic acid: Lithium hydroxide (29.7 mg, 1.24 mmol) was added to a stirred suspension of ethyl 2-(4-(4-((6-(2,6-dichlorophenyl)-5-oxo-5,6-dihydropyrido[4,3-d]pyrimidin-2-yl)amino)phenyl)piperazin-1-yl)acetate (68.7 mg, 0.124 mmol) in methanol (10 mL)/water (15 mL) at RT under nitrogen. After 5 h, the reaction mixture was acidified to pH 3 by addition of 2M HCl (aq) solution. The resultant precipitate was collected by vacuum filtration and washed using water (3×5 mL) and diethyl ether (3×5 mL), successively. The resultant material was freeze-dried to give the title compound (59.5 mg, 91%) as an off-white solid. LCMS (Method A): $R_T$=0.84 min, m/z=525, 527 [M+H]$^+$. $^1$H NMR (500 MHz, methanol-d4): δ 9.20 (s, 1H), 7.70 (br d, 2H), 7.66-7.61 (m, 2H), 7.53 (dd, 1H), 7.48 (d, 1H), 7.06 (d, 2H), 6.60 (s, 1H), 3.65 (s, 2H), 3.45 (s, 8H).

Method 1: Measurement of Wee-1 kinase activity

In the measurement of Wee-1 activity, a commercial peptide Poly(Lys Tyr(4:1)) hydrobromide was purchased from Sigma Aldrich and used as the substrate. Activated Wee-1 kinase was purchased from Invitrogen (PV3817) and an ADP-Glo luminescent kit was purchased from Promega.

All reactions took place in 60 μL volumes in reaction buffer containing 40 mM Tris-HCl and 20 mM magnesium chloride, supplemented with 0.1 mg/mL bovine serum albumin and 2 mM DTT. Compounds were serially diluted in buffer and 5 μL of each concentration pipetted into a white 384 well plate (Sigma Aldrich M6186). A 5 μL aliquot of the Wee-1 enzyme was added to each well and the plate centrifuged for 1 min to ensure mixing of the enzyme and inhibitor.

The plate was incubated at room temperature for 30 minutes before the addition of 2.0 μg/mL of substrate and 30 μM ATP in a 5 μL aliquot. The plate was centrifuged for one minute and incubated for 1 h at RT.

15 μL of ADP-Glo stop reagent was added to each well to quench the reaction and deplete unconverted ATP. The plate was incubated for a further 40 min in the dark at RT.

30 μL of ADP-Glo kinase detection reagent was added to each well, converting ADP to ATP, catalysing the generation of luciferin by luciferase. The plate was shaken for 1 min, and incubated in the dark for an additional hour.

Luminescence from each well was detected using the Biotek Synergy4 HD plate reader and the percentage inhibition of kinase activity calculated for each inhibitor tested. Positive (kinase only) and negative (no kinase) controls were added to each plate to ensure specific interaction of kinase and inhibitor. The $IC_{50}$ concentration for each inhibitor was calculated by plotting the percentage kinase inhibition against concentration of inhibitor and the curve generated by non-linear regression fitting.

Method 2: Determining the effect of compounds on the phosphorylation of cdc2 at Tyr15

The colorectal cancer cell lines HT-29 and HCT-116 were purchased from the ATCC and routinely maintained in McCoy's Medium (Invitrogen) supplemented with 10% Foetal Calf Serum.

The cells were trypsinised from their growing vessel and counted, 100 μL of cell suspension containing 6000 cells was pipetted into black 96 well Co-star plates and incubated overnight to allow adherence to the surface at a temperature of 37° C. and an atmosphere of 5% $CO_2$. Test compounds were formulated in DMSO and diluted in foetal calf serum supplemented medium. Incubating medium was removed by aspiration and diluted drug supplemented medium added to each well.

The plate was returned to the incubator for an additional eight hours at 37° C. and an atmosphere of 5% $CO_2$. Post incubation, the drug supplemented medium was aspirated from each well and the cells were washed once in ice-cold phosphate buffered saline (PBS). 100 μL of cell lysis buffer (Cell Signalling Technologies #9803) containing 20 mM Tris, 150 mM NaCl, 1 mM EDTA, 1 mM EGTA, 1% Triton-X100, 2.5 mM sodium pyrophosphate, 1 mM glycerophosphate, 1 mM $Na_3VO_4$ and 1 μg/mL leupeptin was added to each well of the 96 well plate and incubated at 4° C. for 30 min. The samples on the plate were snap frozen at −80° C. until required.

Immediately before the continuation of the assay, the sample plate was thawed and centrifuged at 4° C. for 10 min and the supernatant transferred to secondary tubes or 96 well plate.

Cell supernatant was mixed in a ratio of 1:1 with sample dilutent buffer and vortexed for one minute. 100 μL of diluted sample was pipetted into pre-coated plates containing a rabbit polyclonal antibody for phospho-cdc2 (Tyr15) (Cell Signalling Technologies PathScan kit #7176). The plate was sealed and incubated overnight at 4° C.

The plate seal was removed and the well contents aspirated, followed by 3×5 min washes with 200 μL of diluted wash buffer. Between each wash the plate was tapped firmly onto blotting paper to ensure the removal of all kit solution. 100 μL of kit detection antibody was added to each well and the plate re-sealed and incubated at 37° C. for 1 h. Post incubation the plate was washed and processed in a similar manner to that previously described.

100 μL of horseradish peroxidise-linked secondary antibody was added to each test well, the plate sealed and incubated for thirty minutes at 37° C. Post incubation, the plate was washed as previously stated, followed by the addition of 100 μL of 3,3',5,5' tetramethylbenzidine (TMB reagent). The plate was sealed and incubated at RT for 30 min.

100 μL of stop solution was added to each well and the underside of the plate wiped with a lint-free tissue, prior to spectrophotometric determination. Absorbance from each well was read at 450 nm within 30 min of the addition of the stop solution.

The percentage of phospho-cdc2 was calculated compared to DMSO control and plotted versus the concentration of inhibitor using GraphPad Prism. Data was fitted using non-linear regression analysis and $IC_{50}$ values generated.

Method for the Determination of CLint Estimates Using Human Liver Microsomes

Test compounds (final concentration=1 μM; final DMSO concentration=0.1%) were incubated in 0.1M phosphate buffer pH 7.4 with human liver microsomes (0.5 mg of protein/mL) at 37° C. Reactions were started by addition of NADPH in 0.1M phosphate buffer pH 7.4 (final concentration 1 mM). 40 μL aliquots were removed at 2, 5, 10, 15, 20, 30, 40 and 50 min. Reactions were quenched in 80 μL of ice-cold methanol. Samples were subsequently frozen overnight then centrifuged at 3500 rpm for 20 min at 4° C. The supernatants were removed and transferred into analytical plates and analysed by LC/MS/MS.

LC/MS/MS Method:

All samples were analysed on a Waters Acquity I-Class coupled to a Waters Xevo TQD mass spectrometer. A Waters BEH C18 2.1×50 mm 1.7 μm column was used and mobile phases were water and methanol containing 0.1% formic acid as modifier. Analysis was by multiple reaction monitoring and conditions were optimised for each test compound.

Data Analyses:

From a plot of ln peak area against time, the gradient of the line is determined. Subsequently, half-life and intrinsic clearance are calculated using the following equations.

$$\text{Eliminated rate constant } (k) = (-\text{ gradient})$$

$$\text{Half life } (t_{1/2}) \text{ (min)} = \frac{0.693}{k}$$

$$\text{Intrinsic Clearance } (CL_{int}) \text{ (μL/min/million cells)} = \frac{V \times 0.693}{t_{1/2}}$$

where $V$ = Incubation volume (μL) / number of cells

Table 2 below highlights the selectivity of a representative compound of the invention against a panel of 50 kinases (assessed using the Invitrogen SelectScreen® Kinase Profiling Service). Unexpectedly, the representative Wee-1 inhibitor according to the the present invention shows greater selectivity than a representative compound described in BMCL, 2005, p 1931.

| | Example 1 | Compound 1 BMCL, 2005, p1931 (Wee-1 IC50 150 nM, Src IC50 6 nM) |
|---|---|---|
| ABL1 | + | + |
| ACVR1B (ALK4) | − | + |
| AKT1 (PKB alpha) | − | − |
| AMPK A1/B1/G1 | − | − |
| AURKA (Aurora A) | − | − |
| BTK | − | + |
| CDK1/cyclin B | − | − |
| CHEK1 (CHK1) | − | − |
| CSNK1G2 (CK1 gamma 2) | − | − |
| CSNK2A1 (CK2 alpha 1) | − | − |
| DYRK3 | − | − |
| EGFR (ErbB1) | − | + |
| EPHA2 | − | + |
| ERBB2 (HER2) | − | − |
| FGFR1 | − | + |
| FLT3 | − | + |
| FRAP1 (mTOR) | − | − |
| GSK3B (GSK3 beta) | − | − |
| IGF1R | − | − |
| IKBKB (IKK beta) | − | − |
| INSR | − | − |
| IRAK4 | − | − |
| JAK3 | − | + |
| KDR (VEGFR2) | − | + |
| KIT | − | + |
| LCK | − | + |
| MAP2K1 (MEK1) | − | − |
| MAP4K4 (HGK) | − | + |
| MAPK1 (ERK2) | − | − |
| MAPK14 (p38 alpha) | − | + |
| MAPK8 (JNK1) | − | − |
| MAPKAPK2 | − | − |
| MARK2 | − | + |
| MET (cMet) | − | − |
| NEK1 | − | − |
| NTRK1 (TRKA) | − | − |
| PAK4 | − | − |
| PDGFRB (PDGFR beta) | − | + |
| PHKG2 | − | − |
| PIM1 | − | − |
| PLK1 | − | − |
| PRKACA (PKA) | − | − |
| PRKCB1 (PKC beta I) | − | − |
| RET | − | + |
| ROCK1 | − | − |
| RPS6KA3 (RSK2) | − | − |
| RPS6KB1 (p70S6K) | − | − |
| SRC | − | + |
| SYK | − | − |
| TEK (Tie2) | − | − |

"−": Inhibition <75% @ 300-350 nM;
"+": Inhibition >75% at 300-350 nM

TABLE 2

Compound 1

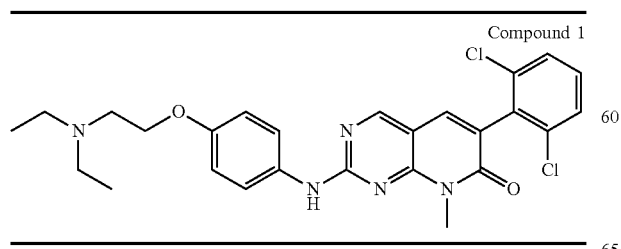

Bioorg. Med. Chem. Lett. 2005, 15, 1931-1935.

The invention claimed is:

1. A compound of Formula (I):

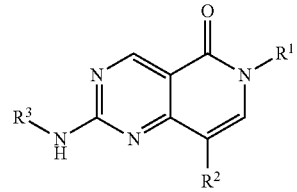

or a pharmaceutically acceptable salt or N-oxide thereof, wherein:
 $R^1$ is a 2,6-dichlorophenyl group;
 $R^2$ is a hydrogen atom;
 $R^3$ is a group represented by the formula (c):

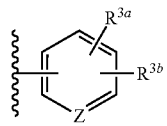

wherein Z is a methine group;
 $R^{3a}$ is a nitrogen-containing heterocyclyl group; and
 $R^{3b}$ is a $C_1$-$C_6$ alkyl group, a $C_2$-$C_6$ alkenyl group, a $C_2$-$C_6$ alkynyl group, or a $C_1$-$C_6$ alkoxy group;
 wherein the $C_1$-$C_6$ alkyl group, the $C_2$-$C_6$ alkenyl group, the $C_2$-$C_6$ alkynyl group, or the $C_1$-$C_6$ alkoxy group is optionally substituted with one or more substituents selected from alkyl, aralkyl, alkenyl, alkynyl, halo, cyano, amino, amido, alkylamino, arylamino, carbocyclyl, cycloalkyl, cycloalkenyl, aryl, nitro, thio, alkanoyl, hydroxy, aryloxy, alkoxy, alkylthio, arylthio, aralkyloxy, aralkylthio, carboxy, alkoxycarbonyl, oxo, alkylsulfonyl and arylsulfonyl.

2. The compound of claim 1, or a pharmaceutically acceptable salt or N-oxide thereof, wherein $R^3$ is a group represented by the formula (e):

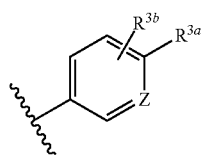

3. The compound of claim 2, or a pharmaceutically acceptable salt or N-oxide thereof, wherein
 $R^{3b}$ is a methoxy group or a $C_1$-$C_2$ alkyl group, wherein the $C_1$-$C_2$ alkyl group is optionally substituted with a substituent selected from the group consisting of hydroxy and amino.

4. The compound of claim 3, wherein $R^{3b}$ is a methoxy group.

5. The compound of claim 1, or a pharmaceutically acceptable salt or N-oxide thereof, wherein the compound is selected from the group consisting of:
 (7) 6- (2,6-dichlorophenyl)-2-((3-methyl-4-(piperazin-1-yl)phenyl)amino)pyrido[4,3-d]pyrimidin-5(6H)-one;

(13) 6-(2,6-dichlorophenyl)-2-((3-methoxy-4-(piperazin-1-yl)phenyl)amino)pyrido[4,3-d]pyrimidin-5(6H)-one;
(18) 6-(2,6-dichlorophenyl)-2-((3-(hydroxymethyl)-4-(piperazin-1-yl)phenyl)amino)pyrido[4,3-d]pyrimidin-5(6H)-one; and
(20) 6-(2,6-dichlorophenyl)-2-((3-((methylamino)methyl)-4-morpholinophenyl)amino)pyrido[4,3-d]pyrimidin-5(6H)-one.

6. A pharmaceutical composition comprising a compound of claim 1, or a pharmaceutically acceptable salt or N-oxide thereof, and at least one pharmaceutically acceptable excipient.

7. The pharmaceutical composition of claim 6, further comprising one or more further pharmaceutically active agents.

8. A method of modulating Wee-1 kinase activity in a human or animal patient in need thereof, comprising administering to the patient an effective amount of a compound of claim 1.

9. The method of claim 8, wherein the human or animal patient suffers from cancer.

10. A compound selected from the group consisting of:
(7) 6-(2,6-dichlorophenyl)-2-((3-methyl-4-(piperazin-1-yl)phenyl)amino)pyrido[4,3-d]pyrimidin-5(6H)-one; and
(13) 6-(2,6-dichlorophenyl)-2-((3-methoxy-4-(piperazin-1-yl)phenyl)amino)pyrido[4,3-d]pyrimidin-5(6H)-one.

11. A compound selected from the group consisting of:
(8) 6-(2,6-dichlorophenyl)-2-((3-(hydroxymethyl)-4-(4-methylpiperazin-1-yl)phenyl)amino)pyrido[4,3-d]pyrimidin-5(6H)-one;
(12) 6-(2,6-dichlorophenyl)-2-((3-methoxy-4-(4-methylpiperazin-1-yl)phenyl)amino)pyrido[4,3-d]pyrimidin-5(6H)-one;
(14) 6-(2,6-dichlorophenyl)-8-(3-hydroxyprop-1-yn-1-yl)-2-((3-methyl-4-(piperazin-1-yl)phenyl)amino)pyrido[4,3-d]pyrimidin-5(6H)-one;
(27) 6-(2,6-dichlorophenyl)-2-((3-chloro-4-(piperazin-1-yl)phenyl)amino)pyrido[4,3-d]pyrimidin-5(6H)-one; and
(29) 6-(2,6-dichlorophenyl)-2-((3-fluoro-4-(piperazin-1-yl)phenyl)amino)pyrido[4,3-d]pyrimidin-5(6H)-one.

* * * * *